US012659893B2

(12) United States Patent
Murphy et al.

(10) Patent No.: US 12,659,893 B2
(45) Date of Patent: Jun. 16, 2026

(54) TECHNIQUE FOR OBTAINING AND PROCESSING A MEASUREMENT OF A BIOSIGNAL

(71) Applicant: CUMULUS NEUROSCIENCE LTD, Belfast (GB)

(72) Inventors: Brian Murphy, Greystones (IE); Yannick Tremblay, Dunmurry (GB); Hugh Nolan, Dublin (IE); Matthew Shaw, Bushmills (GB)

(73) Assignee: CUMULUS NEUROSCIENCE LTD, Belfast (GB)

( * ) Notice: Subject to any disclaimer, the term of this patent is extended or adjusted under 35 U.S.C. 154(b) by 95 days.

(21) Appl. No.: 18/557,914

(22) PCT Filed: Apr. 28, 2021

(86) PCT No.: PCT/EP2021/061155
§ 371 (c)(1),
(2) Date: Oct. 27, 2023

(87) PCT Pub. No.: WO2022/228668
PCT Pub. Date: Nov. 3, 2022

(65) Prior Publication Data
US 2024/0259966 A1     Aug. 1, 2024

(51) Int. Cl.
*H04W 56/00*     (2009.01)
*A61B 5/00*      (2006.01)
*H04W 84/12*     (2009.01)

(52) U.S. Cl.
CPC ........... *H04W 56/001* (2013.01); *A61B 5/002* (2013.01); *A61B 5/6814* (2013.01); *H04W 84/12* (2013.01)

(58) Field of Classification Search
CPC .... H04W 56/001; H04W 84/12; A61B 5/002; A61B 5/6814; A61B 5/0002;
(Continued)

(56) References Cited

U.S. PATENT DOCUMENTS 8,330,596 B2 * 12/2012 Tanaka ............... A61B 5/02438
604/300
9,775,396 B1 * 10/2017 Olivares Velasco ........................
H04B 1/3833
(Continued)

FOREIGN PATENT DOCUMENTS

CN       110916657 A     3/2020
JP       2016158699 A     9/2016

OTHER PUBLICATIONS

The International Search Report and Written Opinion for International Application No. PCT/EP2021/061155 mailed on Feb. 23, 2022.
(Continued)

*Primary Examiner* — Franklin D Balseca
(74) *Attorney, Agent, or Firm* — Womble Bond Dickinson (US) LLP

(57)     ABSTRACT

A head-wearable sensor arrangement for obtaining a measurement of biosignal of a user is provided. The present disclosure also relates to a stimulus-providing wireless mobile device and a computing system. The head-wearable sensor arrangement may send time-stamped medical data comprising a representation of the measurement to the wireless mobile device time-synchronized with the arrangement. The wireless mobile device may send the time-stamped medical data to a computing system. The computing system may process the time-stamped medical data to determine an indicator of health, well-being or performance of the user. The processing may involve decomposing the measurement and using residuals of an autoregressive model or a robust aggregation method on the decomposed measurement.

16 Claims, 14 Drawing Sheets

(58) Field of Classification Search
CPC ... A61B 5/0004; A61B 5/0006; A61B 5/0008;
A61B 5/0015; A61B 5/0022; A61B
5/0024; H04Q 2209/00; H04Q 2209/10;
H04Q 2209/20; H04Q 2209/40; H04Q
2209/43; H04Q 2209/47; H04Q 2209/70;
H04Q 2209/80; H04Q 2209/82; H04Q
2209/823; H04Q 2209/826; H04Q
2209/84; H04Q 2209/88
See application file for complete search history.

(56) References Cited

U.S. PATENT DOCUMENTS

| | | | |
|---|---|---|---|
| 11,438,133 B2 * | 9/2022 | Chen | H04L 41/0853 |
| 11,602,274 B2 * | 3/2023 | Ross | G16H 40/67 |
| 2007/0032737 A1 | 2/2007 | Causevic et al. | |
| 2011/0213278 A1 | 9/2011 | Horak et al. | |
| 2015/0199010 A1 | 7/2015 | Coleman et al. | |
| 2017/0042425 A1 | 2/2017 | Ramlall | |
| 2017/0177023 A1 | 6/2017 | Simon et al. | |
| 2019/0175028 A1 | 6/2019 | Osorio et al. | |
| 2019/0307350 A1 | 10/2019 | Sridhar et al. | |
| 2020/0138318 A1 | 5/2020 | Cardenas et al. | |
| 2020/0337625 A1 | 10/2020 | Aimone et al. | |

OTHER PUBLICATIONS

Navarro X et al: "Denoising preterm EEG by signal decomposition and adaptive filtering: A comparative study", Mar. 1, 2015 (Mar. 1, 2015), pp. 1-13, XP055878948, DOI: 10.1016/j.medengphy.2015. 01.006, located on the Internet at: https://hal.sorbonne-universite. fr/hal-01117143/document.

* cited by examiner

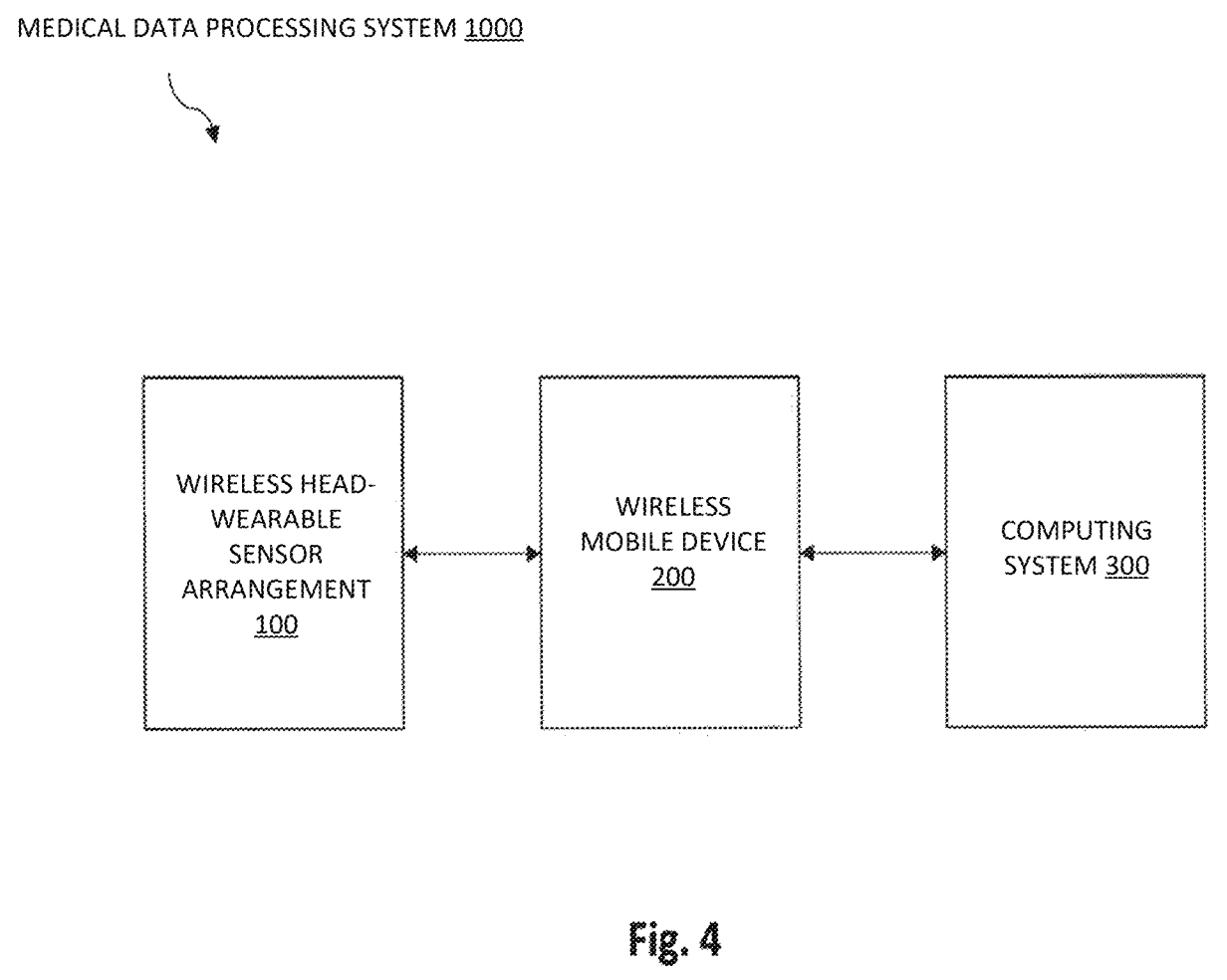

MEDICAL DATA PROCESSING SYSTEM 1000

| WIRELESS HEAD-WEARABLE SENSOR ARRANGEMENT 100 | WIRELESS MOBILE DEVICE 200 | COMPUTING SYSTEM 300 |

Fig. 4

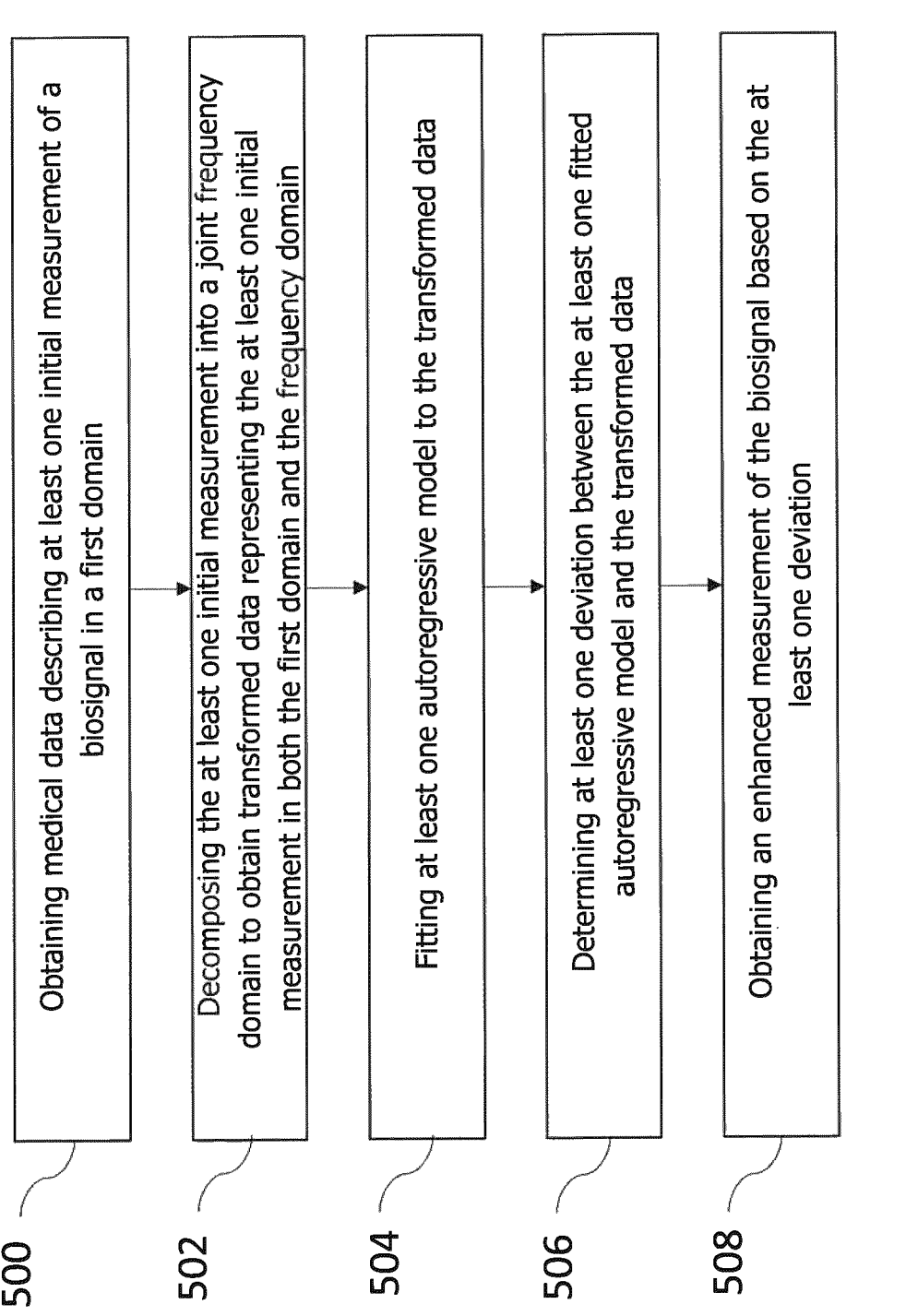

500  Obtaining medical data describing at least one initial measurement of a biosignal in a first domain 502  Decomposing the at least one initial measurement into a joint frequency domain to obtain transformed data representing the at least one initial measurement in both the first domain and the frequency domain 504  Fitting at least one autoregressive model to the transformed data 506  Determining at least one deviation between the at least one fitted autoregressive model and the transformed data 508  Obtaining an enhanced measurement of the biosignal based on the at least one deviation

Fig. 5

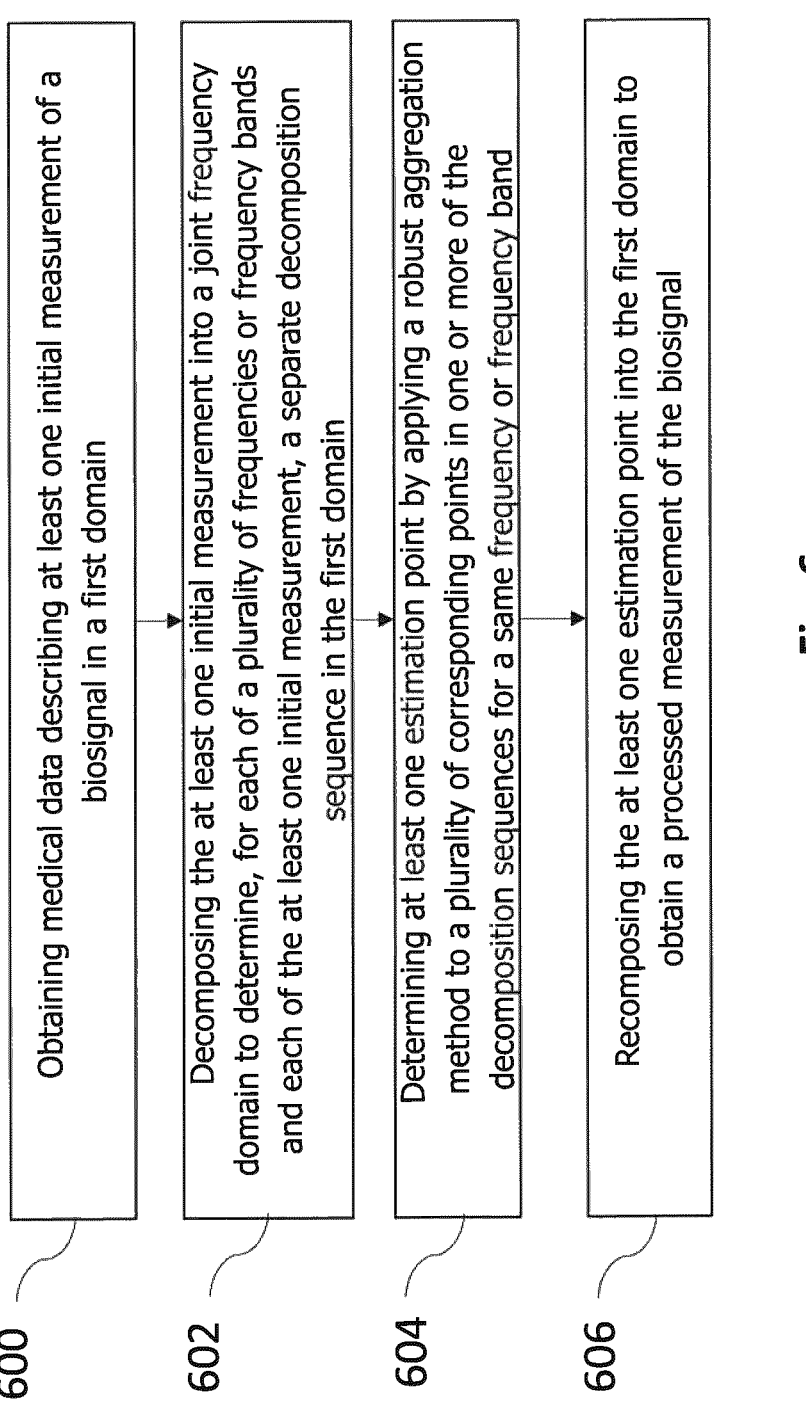

600 Obtaining medical data describing at least one initial measurement of a biosignal in a first domain 602 Decomposing the at least one initial measurement into a joint frequency domain to determine, for each of a plurality of frequencies or frequency bands and each of the at least one initial measurement, a separate decomposition sequence in the first domain 604 Determining at least one estimation point by applying a robust aggregation method to a plurality of corresponding points in one or more of the decomposition sequences for a same frequency or frequency band 606 Recomposing the at least one estimation point into the first domain to obtain a processed measurement of the biosignal

Fig. 6

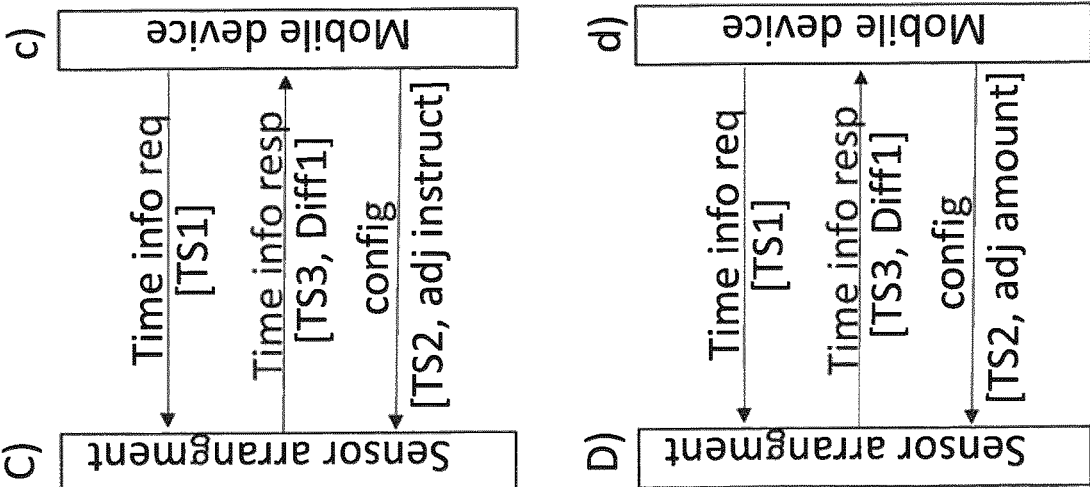
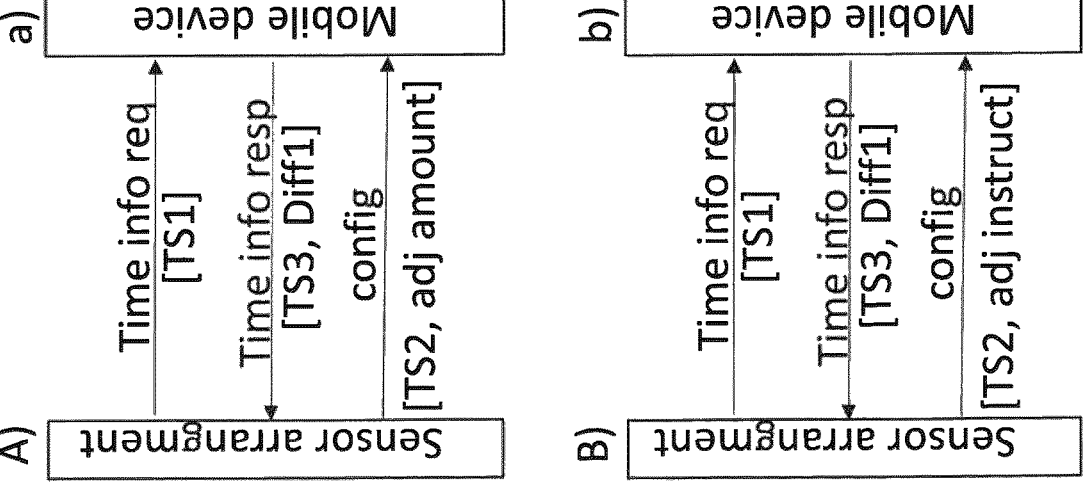
Fig. 7

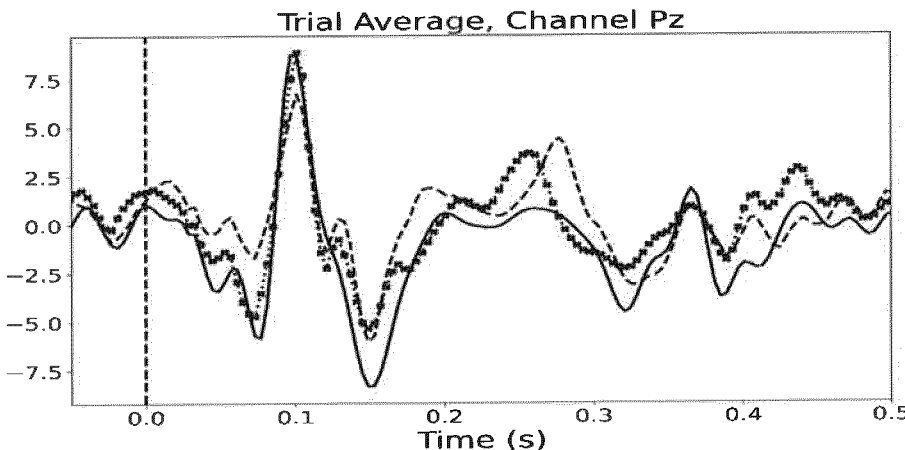
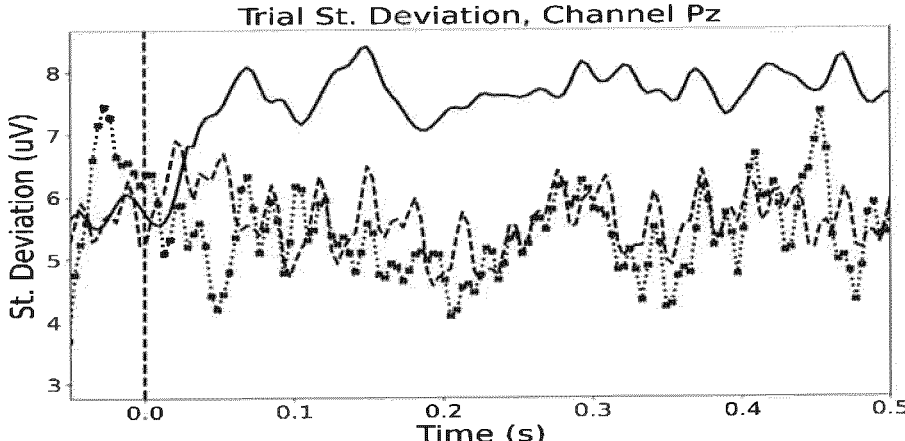
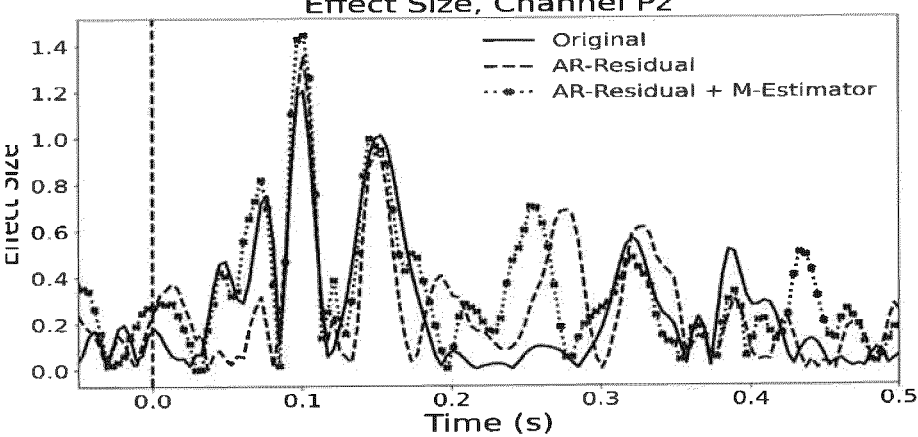
Fig. 14

TECHNIQUE FOR OBTAINING AND PROCESSING A MEASUREMENT OF A BIOSIGNAL

CROSS-REFERENCE TO RELATED APPLICATIONS

This application is a national-phase entry of International Application No. PCT/EP2021/061155 filed on Apr. 28, 2021, the contents of which are incorporated herein by reference in their entirety.

TECHNICAL FIELD

The present disclosure generally relates to sending and processing medical data representative of at least one measurement of a biosignal of a user. A wireless head-wearable sensor arrangement, a wireless mobile device and a computing system are provided. Also provided are methods for obtaining an enhanced measurement and computer program products.

BACKGROUND

Biosignals of a body, for example an electric heart rate signal or an electroencephalographic signal, are of interest for determining or monitoring a state of health, well-being or performance of a human or animal.

In many cases, measurements of biosignals may have low signal-to-noise ratios. This may be disadvantageous for the further processing thereof. For example, it may be desirable to identify relatively short characteristic features (e.g., in the range of 5-20 ms) in a measurement of a biosignal comprising low-frequency noise (e.g., in a frequency band of 10-S0 Hz). In this case, a high-pass filter may be applied to the measurement to obtain an enhanced measurement that has an improved signal-to noise ratio. In some cases, such filtering may not be sufficient. For example, the measurement may comprise relatively short artefacts (e.g., in the range of 5-20 ms) not related to the characteristic features of interest. In these cases, it may be desirable to determine an enhanced measurement in which the characteristic features can be identified more reliably, an amplitude of artefacts is reduced and/or a number of artefacts is reduced.

In case other signals (e.g., user input signals, stimulus signals or else) are used in conjunction with the biosignals, it may be advantageous to know a time-association between such other signals and the biosignals to identify the characteristic features and/or determine the state of health, well-being or performance. In some scenarios, the time-association cannot be reliably predetermined. For example, if a first wireless device is used for obtaining a measurement of a biosignal and a separate, second wireless device is used for obtaining the other signals, it may be desirable to set or obtain the time-association. In some cases, time-association may vary once it has been set due to a relative clock drift between the first and the second wireless device.

In addition to the above, challenges occur when monitoring biosignals of a user in different environments. For instance, the monitoring of EEG signals usually requires a clinical environment with specific test conditions. Such conditions can be cumbersome and unpleasant for the user. On the other hand, performing such measurements in an environment without clinical conditions, such as the home of the user, can cause other challenges, such as high signal noises, artefacts from surroundings, less careful adherence to a task protocol by the user, etc. It is one object to enhance the measurement of a biosignal and enable the monitoring of better signals, even in noisy environments such as the home.

SUMMARY

There is a need for a technique that solves one or more of the aforementioned or other problems.

According to a first aspect, a medical data processing method for obtaining a processed measurement of a biosignal from an initial measurement of the biosignal is provided. The method is performed by a computing system and comprises obtaining medical data describing at least one initial measurement of a biosignal in a first domain, decomposing the at least one initial measurement into a joint frequency domain to obtain transformed data representing the at least one initial measurement in both the first domain and the frequency domain, fitting at least one autoregressive model to the transformed data, determining at least one deviation between the at least one fitted autoregressive model and the transformed data, and obtaining a processed measurement of the biosignal based on the at least one deviation.

According to a second aspect, a computing system is provided. The computing system comprises at least one memory and at least one processor, the at least one memory storing instructions which, when executed on the at least one processor, cause the at least one processor to carry out the method according to the first aspect.

According to a third aspect, a computer program product is provided, comprising program code portions for performing the method of the first aspect when the computer program product is executed on at least one processor. The computer program product may be stored on one or more computer readable recording media.

According to a fourth aspect, a medical data processing method for obtaining a processed measurement of a biosignal from an initial measurement of the biosignal is provided. The method is performed by a computing system and comprises obtaining medical data describing at least one initial measurement of a biosignal in a first domain and decomposing the at least one initial measurement into a joint frequency domain to determine, for each of a plurality of frequencies or frequency bands and each of the at least one initial measurement, a separate decomposition sequence in the first domain. The method further comprises determining at least one estimation point by applying a robust aggregation method to a plurality of corresponding points in one or more of the decomposition sequences for a same frequency or frequency band, and recomposing the at least one estimation point into the first domain to obtain a processed measurement of the biosignal.

According to a fifth aspect, a computing system is provided. The computing system comprises at least one memory and at least one processor, the at least one memory storing instructions which, when executed on the at least one processor, cause the at least one processor to carry out the method according to the fourth aspect. The computing system may be the computing system of the second aspect.

According to a sixth aspect, a computer program product is provided, comprising program code portions for performing the method of the fourth aspect when the computer program product is executed on at least one processor. The computer program product may be stored on one or more computer readable recording media.

According to a seventh aspect, a wireless head-wearable sensor arrangement for sending medical data to a wireless mobile device is provided. The wireless head-wearable sensor arrangement comprises at least one sensor configured to generate at least one measurement of a biosignal of a user wearing the wireless head-wearable sensor arrangement, a first wireless interface, a first clock and a first processor. The first processor is configured to perform a time-synchronization procedure to synchronize the first clock with a second clock of a wireless mobile device or to instruct synchronization of a second clock of a wireless mobile device with the first clock. The first processor is configured to, after having performed the time-synchronization procedure, obtain, from the at least one sensor, the at least one measurement of the biosignal of the user wearing the wireless head-wearable sensor arrangement, allocate at least one time-stamp to the obtained at least one measurement using the first clock, and send medical data via the first wireless interface to the wireless mobile device, the medical data comprising a representation of the at least one measurement and the at least one time-stamp allocated to the at least one measurement.

According to an eighth aspect, a wireless mobile device for receiving medical data from a wireless head-wearable sensor arrangement is provided. The wireless mobile device comprises a second wireless interface, a second clock and a second processor. The second processor is configured to perform a time-synchronization procedure to synchronize the second clock with a first clock of a wireless head-wearable sensor arrangement or to instruct synchronization of a first clock of a wireless head-wearable sensor arrangement with the second clock. The second processor is configured to, after having performed the time-synchronization procedure, receive medical data from the wireless head-wearable sensor arrangement via the second wireless interface and send the medical data to a computing system, the medical data comprising a representation of at least one measurement of a biosignal of a user wearing the wireless head-wearable sensor arrangement and at least one time-stamp allocated to the at least one measurement using the first clock.

According to a ninth aspect, a computing system for receiving medical data from a wireless mobile device is provided. The computing system comprises one or more processors configured to receive, from a wireless mobile device, medical data comprising a representation of at least one measurement of a biosignal of a user wearing a wireless head-wearable sensor arrangement and at least one time-stamp allocated to the at least one measurement using a first clock of the wireless head-wearable sensor arrangement. The one or more processors are configured to determine, based on the representation of the at least one measurement and the at least one time-stamp allocated to the at least one measurement, an indicator of health, well-being or performance of the user of the wireless head-wearable sensor arrangement. The one or more processors may be configured to perform the method according to at least one of the first aspect and the fourth aspect.

According to a tenth aspect, a medical data processing system is provided. The medical data processing system comprises at least two of the following: a wireless head-wearable sensor arrangement: a wireless mobile device; and a computing system, wherein the wireless head-wearable sensor arrangement is the arrangement according to the seventh aspect, the wireless mobile device is the device according to the eighth aspect and/or the computing system is the system according to the ninth aspect.

According to the present disclosure, the at least one (e.g., initial) measurement may be one of an electrical, magnetic, optical or acoustical (e.g., ultrasonic) measurement of the biosignal of the user. The at least one (e.g., initial) measurement may comprise a first-domain (e.g., time-domain) representation and/or a frequency domain representation of the biosignal. The biosignal may be a signal generated by the user's body. The biosignal may be a signal representing a cognitive state of the user. The biosignal may be a neuro-functional signal. The cognitive state may comprise one or more of a feeling of the user, a response to a stimulus provided to the user, a memory performance of the user and a cognitive performance of the user. The biosignal may be a bioelectrical signal, for example an electroencephalographic, EEG, signal. The biosignal may be an acoustic signal, for example an acoustic heart beat signal. The biosignal may be a motion signal of the user's body (e.g., an electric muscle movement signal, or a physical body movement signal for example detectable with an accelerometer). The term medical data may not be limited to data used in a clinical context. The user may be a (e.g., healthy or unhealthy) human or animal. The at least one measurement may be generated and/or obtained while the user is in a non-clinical environment, for example at home.

BRIEF DESCRIPTION OF THE DRAWINGS

Further details, advantages and aspects of the present disclosure will become apparent from the following embodiments taken in conjunction with the drawings, wherein:

FIG. 4 shows an embodiment of a medical data processing system in accordance with the present disclosure:

FIG. 5 shows an embodiment of a first method in accordance with the present disclosure;

FIG. 6 shows an embodiment of a first method in accordance with the present disclosure:

FIG. 7 shows four exemplary time-synchronization procedures in accordance with the present disclosure:

FIG. 14 shows an EEG signal and recomposed residuals, each averaged across the plurality of segments shown in FIG. 8. Also shown are recomposed results of an M-estimator applied to the decomposed residuals.

DETAILED DESCRIPTION

Figure 1:
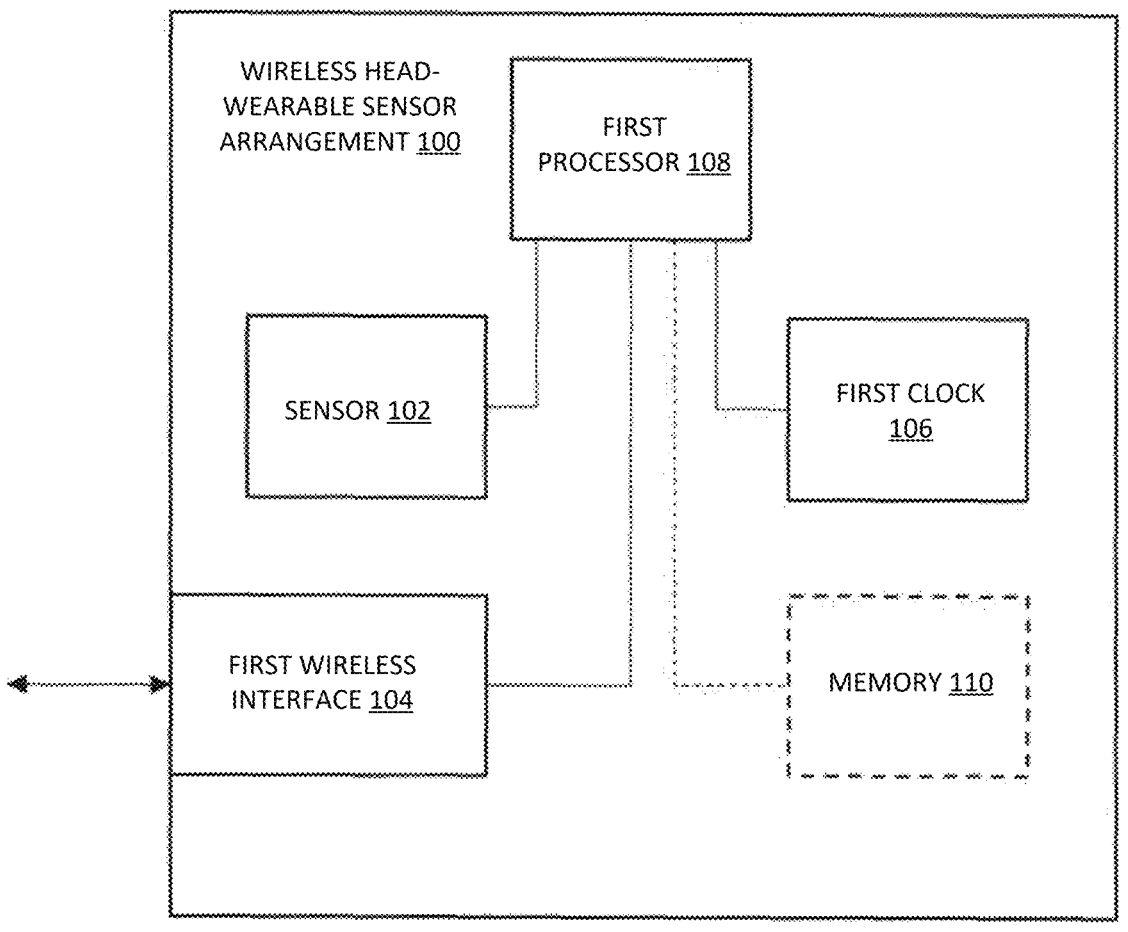
FIG. 1 shows an embodiment of a wireless head-wearable sensor arrangement in accordance with the present disclosure.

In the following description, exemplary embodiments of a wireless head-wearable sensor arrangement will be explained with reference to the drawings. The same reference numerals will be used to denote the same or similar structural features.

Wireless Head-Wearable Sensor Arrangement

FIG. 1 shows a first embodiment of a wireless head-wearable sensor arrangement 100 in accordance with the present disclosure. The wireless head-wearable sensor arrangement 100 is configured for sending medical data to a wireless mobile device. The wireless head-wearable sensor arrangement 100 comprises at least one sensor 102 configured to generate (e.g., record) at least one measurement of a biosignal of a user wearing the wireless head-wearable sensor arrangement 100, a first wireless interface 104, a first clock 106 and a first processor 108. The wireless head-wearable sensor arrangement 100 may further comprise a memory 110 comprising instructions which, when performed by the first processor 108, configure the first processor 108 as described herein. The wireless head-wearable sensor arrangement 100 may for example be a headset, a headband or a helmet.

The first processor 108 is configured to perform a time-synchronization procedure to synchronize the first clock 106 with a second clock of a wireless mobile device (e.g., based on time information received from the wireless mobile device via the first wireless interface 104) or to instruct (e.g., trigger, initiate or enable) synchronization of a second clock of a wireless mobile device with the first clock 106 (e.g., by sending time information to the wireless mobile device via the first wireless interface 104). The first processor 108 is configured to, after having performed the time-synchronization procedure, obtain, from the at least one sensor 102, the at least one measurement of the biosignal of the user wearing the wireless head-wearable sensor arrangement, allocate at least one time-stamp to the obtained at least one measurement (e.g., using the first clock 106), and send medical data via the first wireless interface 104 to the wireless mobile device, the medical data comprising a representation of the at least one measurement and the at least one time-stamp allocated to the at least one measurement.

The first processor 108 may be configured to store the medical data in the memory 110 or in a physically removable memory (e.g., a storage card, a USB stick or the like), for instance, but not exclusively for the case in which the medical data cannot be sent to the wireless mobile device via the first wireless interface 103.

The at least one sensor 102 may be or comprise an electrode (for instance a dry electrode) and may be configured to generate a measurement of the bioelectric signal. The biosignal may be an acoustic signal, for example an acoustic heart beat signal. The at least one sensor may be or comprise a microphone and may be configured to generate a measurement of the acoustic signal.

The first wireless interface 104 may be a wireless local area network (WLAN) interface, a WiFi interface (e.g., according to the standard IEEE 802.11), a Bluetooth interface or another radio interface (e.g., a 4G- or SG-interface). The first wireless interface 104 may comprise at least one of a WLAN interface, a WiFi interface and a Bluetooth interface. The first processor 108 may comprise a plurality of processing units. For example, the first processor 108 may be implemented as a multi-core processor or as a distributed processor. The arrangement 100 may comprise at least one of a Real Time Clock, RTC, chip and an oscillator circuit, configured as the first clock 106. The first clock 106 may be configured to provide the first processor 108 with a current time. The first processor 108 may be configured to use the time provided by the first clock 106 to generate a time-stamp of the current time. The first clock 106 and the first processor 108 may be part of a same integrated circuit or computer chip.

The first processor 108 or the at least one sensor 102 may be configured to determine the representation of the at least one measurement based on the at least one measurement. The representation of the at least one measurement may correspond to, consist of or comprise the at least one measurement. The representation of the at least one measurement may comprise or consist of a digitized or numerical conversion of the at least one measurement, or a (e.g., frequency-, amplitude- and/or noise-) filtered version of the at least one measurement.

Time-Synchronization Procedure

The first processor 108 may be configured to perform the time-synchronization procedure such that (e.g., at least at a time of starting the generation or the obtaining of the at least one measurement) the first clock 106 runs synchronous with the second clock. The first processor 108 may be configured to perform the time-synchronization procedure such that the first clock 106 and the second clock are synchronized with one another (e.g., at least at a time of starting the generation or the obtaining of the at least one measurement). Synchronizing the first clock 106 with the second clock may comprise adjusting the first clock 106 to the second clock, for example as described below for examples A) or C). Synchronizing the first clock with the second clock may comprise adjusting the first clock 106 such that a difference between a time provided by the first clock 106 and a time provided by the second clock at the same point in time is compensated, eliminated, minimized (e.g., falls below a predefined tolerance level such as 1 ms, Sms or !Oms) or essentially zero (e.g., falls below a predefined tolerance level such as 1 ms, 2 ms or 3 ms). The term "running synchronous" as used herein means that a time misalignment or difference between a time provided by the first clock 106 and a time provided by the second clock at the same point in time is below a predefined tolerance level such as 1 ms, Sms or !Oms or is essentially zero (e.g., is below a predefined tolerance level such as O.1 ms, O.Sms or 1 ms). Instructing synchronization of the second clock with the first clock 106 may comprise instructing (e.g., a second processor of) the wireless mobile device to adjust the second clock to the first clock 106, for example as described below for examples B) or D). Instructing synchronization of the second clock with the first clock 106 may comprise instructing (e.g., a second processor of) the wireless mobile device to adjust the second clock such that a difference between a time provided by the second clock and a time provided by the first clock 106 at the same point in time is compensated, eliminated, minimized (e.g., falls below a predefined tolerance level such as 1 ms, Sms or !Oms) or essentially zero (e.g., falls below a predefined tolerance level such as 1 ms, 2 ms or 3 ms).

Time-Stamp

The at least one time-stamp may be or may have been generated using the first clock 106, for example based on a time provided by the first clock 106. The at least one time-stamp allocated to the obtained at least one measurement may indicate a time of starting the generation of the at least one measurement by the at least one sensor 102 and/or a time of starting the obtaining of the at least one measurement by the first processor 108. Alternatively or additionally, the at least one time-stamp allocated to the obtained at least one measurement may indicate a time of ending the generation of the at least one measurement by the at least one sensor 102 and/or a time of ending the obtaining of the at least one measurement by the first processor 108. The at least one time-stamp may be generated by the first processor 108 at regular intervals using the first clock 106. The at least one time-stamp may be allocated to the at least one measurement by time-stamping the at least one measurement with the at least one time-stamp, including the at least one time-stamp in the at least one measurement and/or determining a time-association between the at least one measurement and the at least one time-stamp.

Packet Numbers

The first processor 108 may divide the medical data into a plurality of data packets, and assign a packet number to each data packet. The packet number may indicate a relative position of the packet in the medical data or the at least one measurement. Each data packet may comprise a part of the at least one measurement and the packet number may indicate which part of the at least one measurement is included in the packet. The data packets may be separately sent to the wireless mobile device. The data packets may later, e.g. after being received by the wireless mobile device, be re-ordered based on the packet numbers (e.g., by a second processor of the wireless mobile device).

Time Information

The time information sent to the wireless mobile device by the first processor 108 may comprise time information of the first clock 106, for example a time-stamp generated using the first clock 106. The time information received from the wireless mobile device by the first processor 108 may comprise time information of the second clock, for example a time-stamp generated using the second clock. The time information received from or sent to the wireless mobile device by the first processor 108 may comprise at least one of a time synchronization request message, a time information request message, a time information response message, a configuration message, or information comprised therein, as for example described below with reference to examples A) to D).

Start Message

The first processor 108 may be configured to receive a start message from the wireless mobile device (e.g., via the first wireless interface 104) and instruct the at least one sensor to generate the at least one measurement in response to receiving the start message. The first processor 108 may be configured to receive a start message from the wireless mobile device (e.g., via the first wireless interface 104) and start obtaining the at least one measurement in response to receiving the start message or based on a time specified in the start message. The first processor 108 may be configured to start obtaining the at least one measurement in response to sending a start message to the wireless mobile device or in response to receiving a start message from the wireless mobile device. The start message may correspond to the configuration message as described herein.

Repeat Time-Synchronization Procedure

The first processor 108 may be configured to repeat the time-synchronization procedure at predetermined time points, periodically and/or after having obtained the at least one measurement. The first processor 108 may be configured to send an indication of an adjustment amount of the first clock 106 to the wireless device. The adjustment amount may be the time amount with which the first clock 106 is adjusted by the first processor 108 during the (e.g., initial or repeated) time-synchronization procedure.

Examples A), B), C) and D) of Time-Synchronization Procedure

Four examples A). B). C) and D) of how the time-synchronization procedure may be performed by the first processor 108 will now be described. The first processor 108 may be configured to perform the time-synchronization according to one of examples A) to D) and, when repeating the time-synchronization, perform the time-synchronization according to the same or another one of examples A) to D). It is noted that arrangement 100 according to example A) described below may be configured to perform the time-synchronization procedure with the device according to example a) described below with reference to FIG. 2. The arrangement 100 according to example B) described below may be configured to perform the time-synchronization procedure with the device according to example b) described below with reference to FIG. 2. The same applies to examples C) and c), and examples D) and d) described herein.

According to example A) and example B) of the first aspect, the first processor 108 may be configured to perform the time-synchronization procedure by sending a time information request message to the wireless mobile device via the first wireless interface 104, the time information request message comprising a first time-stamp (e.g., generated using the first clock 106) of the time of sending the time information request message, and receiving a time information response message from the wireless mobile device via the first wireless interface 104, the time information response message comprising synchronization information.

According to example A), the first processor 108 may be configured to synchronize the first clock 106 by adjusting the first clock 106 based at least on the synchronization information. The first processor 108 may be configured to, after having adjusted the first clock 106, send a configuration message (e.g., the start message) to the wireless mobile device via the first wireless interface 104, the configuration message comprising at least one of a second time-stamp (e.g., generated using the first clock 106) of the time of sending the configuration message and an indication of an adjustment amount of the first clock 106.

According to example B), the first processor 108 may be configured to determine an adjustment amount instruction for the second clock based on the synchronization information and send a configuration message to the wireless mobile device (e.g., via the first wireless interface 104) comprising the adjustment amount instruction for the second clock and, optionally, a second time-stamp of the time of sending the configuration message. The adjustment amount instruction for the second clock may instruct the wireless mobile device to adjust the second clock with a time amount defined by the adjustment amount instruction.

According to example C) and example D) of the first aspect, the first processor 108 may be configured to perform the time-synchronization procedure by receiving a time information request message from the wireless mobile device via the first wireless interface 104, the time information request message comprising a first time-stamp (e.g., generated using the second clock) of the time of sending the time information request message, determining synchronization information based at least on information comprised in the time information request message, and sending a time information response message to the wireless mobile device via the first wireless interface 104, the time information response message comprising the synchronization information.

According to example C), the first processor 108 may be configured to, after having sent the time information response message, receive a configuration message (e.g., the start message) from the wireless mobile device via the first wireless interface 104, and adjust the first clock 106 based on information comprised in the configuration message. The information comprised in the configuration message may comprise at least one of a second time-stamp (e.g., generated using the second clock) of the time of sending the configuration message and an adjustment amount instruction for the first clock 106, wherein the adjustment amount instruction for the first clock 106 may be based on the synchronization information. The adjustment amount instruction for the first clock 106 may instruct the first processor 108 to adjust the first clock 106 with a time amount defined by the adjustment amount instruction.

According to example D), the first processor 108 is configured to, after having sent the time information response message, receive a configuration message from the wireless mobile device via the first wireless interface 104, the configuration message comprising an indication of an adjustment amount of the second clock and, optionally, a second time-stamp (e.g., generated using the second clock) of the time of sending the configuration message.

Synchronization Information

In any one of examples A), B), C) or D), the synchronization information may be dependent on at least the first time-stamp. The synchronization information may comprise an indication of a first time difference between the time of sending the time information request message as indicated by the first time-stamp and a time of receiving the time information request message. The synchronization information may be dependent on at least the first time-stamp by comprising the indication of the first time difference. The synchronization information may comprise a third time-stamp of a time of sending the time information response message. The indication of the first time difference may consist of the first time-stamp and the third time-stamp or be an indication of a time difference between the time indicated by the first time-stamp and the time indicated by the third time-stamp.

Synchronization Deviation

According to example A) or B), the first processor 108 may be configured to determine a synchronization deviation between the first clock 106 and the second clock based on the first time difference and a second time difference between the time of sending the time information response message as indicated by the third time-stamp and a time of receiving the time information response message. The first processor 108 may be configured to determine a round-trip latency based on the first time difference and the second time difference, and determine the synchronization deviation further based on the round-trip latency. The synchronization deviation may be a (e.g., momentary) difference between a time provided by the first clock 106 and a time provided by the second clock (e.g., at a particular point in time or during a predefined time interval). The round-trip latency may be an indication of a travel time of a message from the arrangement to the wireless device (e.g., and back).

Clock Adjustment Based on Synchronization Deviation

According to example A), the first processor 108 may be configured to synchronize the first clock 106 by adjusting the first clock 106 such that the determined synchronization deviation is eliminated, minimized (e.g., falls below a predefined tolerance level such as 1 ms, Sms or 10 ms) or compensated. The first processor 108 may be configured to perform multiple cycles of sending the time information request message and receiving the time information response message, determine the synchronization deviation for each pair of time information request message and time information response message, and adjust the first clock 106 such that a smallest of the determined synchronization deviations is eliminated, minimized or compensated, or such that an average of the determined synchronization deviations is eliminated, minimized or compensated.

According to example B), the first processor 108 may be configured to determine the adjustment amount instruction for the second clock to instruct the wireless mobile device to adjust the second clock such that the determined synchronization deviation is eliminated, minimized (e.g., falls below a predefined tolerance level such as 1 ms, Sms or 10 ms) or compensated. The first processor 108 may be configured to perform multiple cycles of sending the time information request message and receiving the time information response message, determine the synchronization deviation for each pair of time information request message and time information response message, and determine the adjustment amount instruction for the second clock to instruct the wireless mobile device to adjust the second clock such that a smallest of the determined synchronization deviations is eliminated, minimized or compensated, or such that an average of the determined synchronization deviations is eliminated, minimized or compensated.

First Variant for Synchronization Initiation

In a first variant (e.g., of any one of examples A) to D)), the first processor 108 may be configured to receive a time synchronization request message from the wireless mobile device via the first wireless interface 104 and to start performing the time-synchronization procedure in response to (e.g., responsive to or triggered by) receiving the time synchronization request message. The time synchronization request message may comprise a fourth time-stamp (e.g., generated using the second clock) of a time of sending the time synchronization request message and the first processor 108 may be configured to pre-adjust the first clock 106 based on the time of sending the time synchronization request message as indicated by the fourth time-stamp, before performing the time-synchronization procedure. The first processor 108 may be configured to pre-adjust the first clock 106 such that its time corresponds to the time indicated by the fourth time-stamp. The first processor 108 may be configured to pre-adjust the first clock 106 if the time indicated by the fourth time-stamp deviates more than a predefined amount (e.g., 1 s, Ss or 10 s) from a time of receiving the time synchronization request message (e.g., determined using the first clock 106).

Second Variant for Synchronization Initiation

In a second variant (e.g., of any one of examples A) to D)), the first processor 108 may be configured to send a time synchronization request message to the wireless mobile device via the first wireless interface 104 to trigger (e.g., instruct or initiate) the wireless mobile device to start performing a time-synchronization procedure. The time synchronization request message may comprise a fourth time-stamp (e.g., generated using the first clock 106) of a time of sending the time synchronization request message and instruct the wireless mobile device to pre-adjust the second clock based on the time of sending the time synchronization request message as indicated by the fourth time-stamp, before performing the time-synchronization procedure. The time synchronization request message may instruct the wireless mobile device to pre-adjust the first clock 106 such that its time corresponds to the time indicated by the fourth time-stamp. The time synchronization request message may instruct the wireless mobile device to pre-adjust the second clock if the time indicated by the fourth time-stamp deviates more than a predefined amount (e.g., 1 s, Ss or 10 s) from a time of receiving the time synchronization request message (e.g., determined using the second clock).

Wireless Mobile Device

Figure 2:
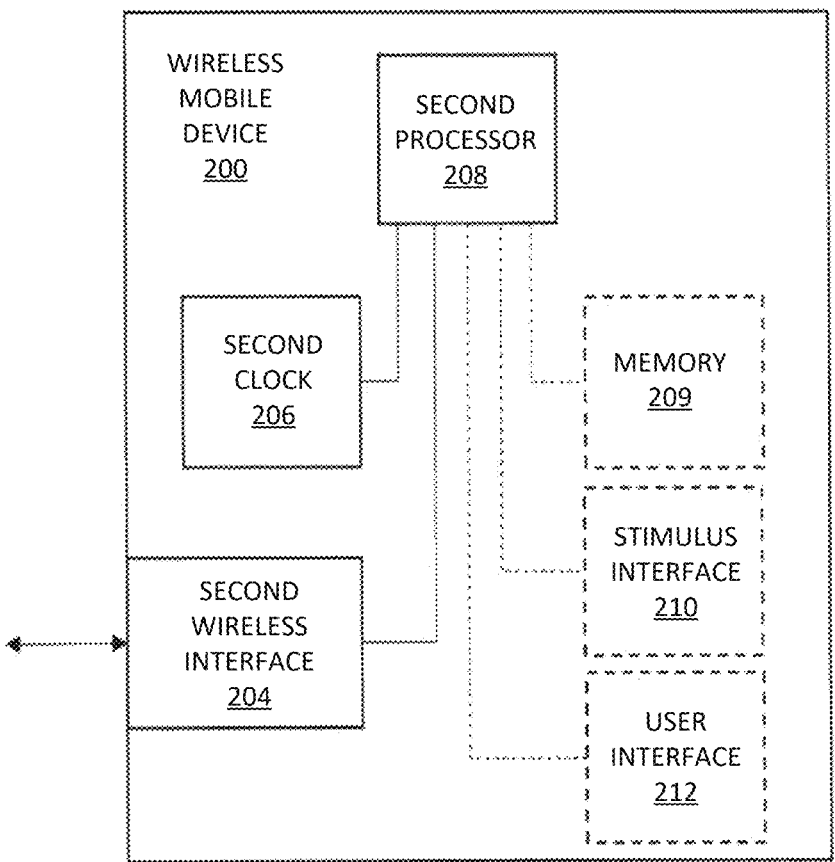
FIG. 2 shows an embodiment of a wireless mobile device in accordance with the present disclosure.

FIG. 2 shows a first embodiment of a wireless mobile device 200 in accordance with the present disclosure. The wireless mobile device 200 comprises a second wireless interface 204, a second clock 206 and a second processor 208. The wireless mobile device 200 may be the wireless mobile device referred to above under the discussion of FIG. 1. The wireless mobile device 200 may further comprise a memory 209 comprising instructions which, when performed by the second processor 208, configure the second processor 208 as described herein. The wireless mobile device 200 may for example be a tablet, a laptop or a smartphone.

The second processor 208 is configured to perform a time-synchronization procedure to synchronize the second clock 206 with a first clock (e.g., the first clock 106) of a wireless head-wearable sensor arrangement (e.g., the arrangement 100) or to instruct (e.g., trigger, initiate or enable) synchronization of a first clock (e.g., the first clock 106) of a wireless head-wearable sensor arrangement (e.g., the arrangement 100) with the second clock (e.g., by sending time information to the wireless head-wearable sensor arrangement via the second wireless interface). The second processor 208 is configured to, after having performed the time-synchronization procedure, receive medical data from the wireless head-wearable sensor arrangement via the second wireless interface 204 and send the medical data to a computing system, the medical data comprising a representation of at least one measurement of a biosignal of a user wearing the wireless head-wearable sensor arrangement and at least one time-stamp allocated to the at least one measurement. The second processor 208 may be configured to perform the time-synchronization procedure to synchronize the second clock 206 with the first clock based on time information received from the wireless head-wearable sensor arrangement via the second wireless interface.

The second wireless interface 204 may be a wireless local area network, WLAN, interface, a WiFi interface (e.g., according to the standard IEEE 802.11), a Bluetooth interface or another radio interface (e.g., a 4G- or SG-interface). The second wireless interface 204 may comprise at least one of a WLAN interface, a WiFi interface and a Bluetooth interface. The second processor 208 may comprise a plurality of processing units. For example, the second processor 208 is implemented as a multi-core processor or as a distributed processor. The device 200 may comprise at least one of a Real Time Clock, RTC, chip and an oscillator circuit, configured as the second clock 206. The second clock 206 may be configured to provide the second processor 208 with a current time. The second processor 208 may be configured to use the time provided by the second clock 206 to generate a time-stamp of the current time. The second clock 206 and the second processor 208 may be part of a same integrated circuit or computer chip.

As noted with reference to FIG. 1, the representation of the at least one measurement may correspond to, consist of or comprise the at least one measurement. The representation of the at least one measurement may comprise or consist of a digitized or numerical conversion of the at least one measurement, or a (e.g., frequency-, amplitude- and/or noise-) filtered version of the at least one measurement.

The second processor 208 may be configured to perform the time-synchronization procedure such that (e.g., at least at a time the at least one measurement is generated) the second clock 206 runs synchronous with the first clock. The second processor 208 may be configured to perform the time-synchronization procedure such that the second clock 206 and the first clock are synchronized with one another (e.g., at least at a time of starting the generation of the at least one measurement). Synchronizing the second clock 206 with the first clock may comprise adjusting the second clock 206 to the first clock, for example as described below for examples B) or D). Synchronizing the second clock 206 with the first clock may comprise adjusting the second clock 206 such that a difference between a time provided by the second clock 206 and a time provided by the first clock at the same point in time is compensated, eliminated, minimized (e.g., falls below a predefined tolerance level such as 1 ms, Sms or 10 ms) or essentially zero (e.g., falls below a predefined tolerance level such as 1 ms, 2 ms or 3 ms). As noted above, the term "running synchronous" as used herein means that a time misalignment or difference between a time provided by the first clock and a time provided by the second clock 206 at the same point in time is below a predefined tolerance level such as 1 ms, Sms or 10 ms or is essentially zero (e.g., is below a predefined tolerance level such as 0.1 ms, 0.Sms or 1 ms). Instructing synchronization of the first clock with the second clock 206 may comprise instructing (e.g., a first processor of) the wireless head-wearable sensor arrangement to adjust the first clock to the second clock 206, for example as described below for examples A) or C). Instructing synchronization of the first clock with the second clock 206 may comprise instructing (e.g., a first processor of) the wireless head-wearable sensor arrangement to adjust the first clock such that a difference between a time provided by the first clock and a time provided by the second clock 206 at the same point in time is compensated, eliminated, minimized (e.g., falls below a predefined tolerance level such as 1 ms, Sms or 10 ms) or essentially zero (e.g., falls below a predefined tolerance level such as 1 ms, 2 ms or 3 ms).

Time-Stamp

The at least one time-stamp may be or may have been generated using the first clock, for example based on a time provided by the first clock. The at least one time-stamp allocated to the obtained at least one measurement may indicate a time of starting a generation of the at least one measurement by at least one sensor (e.g., the at least one sensor 102) comprised in the wireless head-wearable sensor arrangement and/or a time of starting an obtaining of the at least one measurement by a first processor (e.g., the first processor 108) of the wireless head-wearable sensor arrangement from the at least one sensor. Alternatively or additionally, the at least one time-stamp allocated to the obtained at least one measurement may indicate a time of ending the generation of the at least one measurement and/or a time of ending the obtaining of the at least one measurement. The at least one time-stamp may be generated at regular intervals using the first clock. The at least one time-stamp may be allocated to the at least one measurement by time-stamping the at least one measurement with the at least one time-stamp, including the at least one time-stamp in the at least one measurement and/or determining a time-association between the at least one measurement and the at least one time-stamp.

Packet Numbers

The received medical data may be divided into a plurality of data packets (e.g., by the wireless head-wearable sensor arrangement), and a packet number may be assigned to each data packet. The packet number may indicate a relative position of the packet in the medical data or the at least one measurement. Each data packet may comprise a part of the at least one measurement and the packet number may indicate which part of the at least one measurement is included in the packet. The data packets may be separately received by the wireless mobile device 200. The data packets may, after being received by the wireless mobile device 200, be re-ordered based on the packet numbers (e.g., by the second processor 208 of the wireless mobile device) to obtain the medical data in the correct form. That is, the second processor 208 may re-order the received data packets such that the order complies with the packet numbers. This may ensure that the parts of the at least one measurement comprised in the packets are joined in the correct sequence.

The second processor 208 may send the medical data to the computing system in the form of one of more packets, the packets having (e.g., unique or ascending) packet numbers and each packet comprising a part of the at least one measurement.

The data packets received by the wireless device 208 may be the same as the data packets sent to the computing system. Alternatively, the second processor 208 may be configured to divide the medical data into a different plurality of packets.

Time Information

The time information sent to the wireless head-wearable sensor arrangement by the second processor 208 may comprise time information of the second clock 206, for example a time-stamp generated using the second clock 206. The time information received from the wireless head-wearable sensor arrangement by the second processor 208 may comprise time information of the first clock, for example a time-stamp generated using the first clock. The time information received from or sent to the wireless head-wearable sensor arrangement by the second processor 208 may comprise at least one of a time synchronization request message, a time information request message, a time information response message, a configuration message, or information comprised therein, as for example described below with reference to examples a) to d).

Start Message

The second processor 208 may be configured to send a start message to the wireless head-wearable sensor arrangement (e.g., via the second wireless interface 204) instructing the wireless head-wearable sensor arrangement to start generating or obtaining the at least one measurement. The start message may correspond to the configuration message as described herein.

Examples a), b), c) and d) of Time-Synchronization Procedure

Four examples a), b), c) and d) of how the time-synchronization procedure may be performed by the second processor 208 will now be described. The second processor 208 may be configured to perform the time-synchronization according to one of examples a) to d) and, when repeating the time-synchronization, perform the time-synchronization according to the same or another one of examples a) to d). It is noted that device 200 according to example a) described below may be configured to perform the time-synchronization procedure with the arrangement according to example A) described above with reference to FIG. 1. The device 200 according to example b) described below may be configured to perform the time-synchronization procedure with the arrangement according to example B) described above with reference to FIG. 1. The same applies to examples c) and C) and examples d) and D) described herein.

In example a) and example b), the second processor 208 is configured to receive a time information request message from the wireless head-wearable sensor arrangement via the second wireless interface, the time information request message comprising a first time-stamp (e.g., generated using the first clock) of the time of sending the time information request message, determine synchronization information based at least on information comprised in the time information request message, and send a time information response message to the wireless head-wearable sensor arrangement via the second wireless interface, the time information response message comprising the synchronization information.

In example a), the second processor 208 may be configured to, after having sent the time information response message, receive a configuration message (e.g., the start message) from the wireless head-wearable sensor arrangement via the second wireless interface 204, the configuration message comprising an indication of an adjustment amount of the first clock and, optionally, a second time-stamp (e.g., generated using the first clock) of the time of sending the configuration message.

In example b), the second processor 208 may be configured to, after having sent the time information response message, receive a configuration message from the wireless head-wearable sensor arrangement via the second wireless interface, and adjust the second clock based on information comprised in the configuration message. The information comprised in the configuration message may comprise at least one of a second time-stamp (e.g., generated using the first clock) of the time of sending the configuration message and an adjustment amount instruction for the second clock, wherein the adjustment amount instruction for the second clock may be based on the synchronization information. The adjustment amount instruction may instruct the second processor 208 to adjust the second clock 206 with an adjustment amount specified by the adjustment amount instruction.

In example c) and example d) of the second aspect, the second processor 208 may be configured to send a time information request message to the wireless head-wearable sensor arrangement via the second wireless interface, the time information request message comprising a first time-stamp (e.g, generated using the second clock 206) of the time of sending the time information request message, and receive a time information response message from the wireless head-wearable sensor arrangement via the second wireless interface, the time information response message comprising synchronization information.

In example c), the second processor 208 may be configured to determine an adjustment amount instruction for the first clock based on the synchronization information and send a configuration message to the wireless head-wearable sensor arrangement comprising the adjustment amount instruction for the first clock and, optionally, a second time-stamp of the time of sending the configuration message. The adjustment amount instruction for the first clock may instruct the wireless head-wearable sensor arrangement to adjust the first clock with a time amount defined by the adjustment amount instruction.

In example d), the second processor 208 may be configured to synchronize the second clock by adjusting the second clock based at least on the synchronization information. The second processor 208 may be configured to, after having adjusted the second clock, send a configuration message to the wireless head-wearable sensor arrangement via the second wireless interface, the configuration message comprising at least one of a second time-stamp of the time of sending the configuration message and an indication of an adjustment amount of the second clock.

In any one of examples a), b), c) or d), the synchronization information may be dependent on at least the first time-stamp. The synchronization information may comprise an indication of a first time difference between the time of sending the time information request message as indicated by the first time-stamp and a time of receiving the time information request message. The synchronization information may be dependent on at least the first time-stamp by comprising the indication of the first time difference. The synchronization information may comprise a third time-stamp of a time of sending the time information response message. The indication of the first time difference may consist of the first time-stamp and the third time-stamp or be an indication of a time difference between the time indicated by the first time-stamp and the time indicated by the third time-stamp.

Synchronization Deviation

In example c) or exampled), the second processor 208 may be configured to determine a synchronization deviation between the first clock and the second clock based on the first time difference and a second time difference between the time of sending the time information response message as indicated by the third time-stamp and a time of receiving the time information response message. The second processor 208 may be configured to determine a round-trip latency based on the first time difference and the second time difference, and determine the synchronization deviation further based on the round-trip latency. The synchronization deviation may be a (e.g., momentary) difference between a time provided by the first clock and a time provided by the second clock (e.g., at a particular point in time or during a predefined time interval). The round-trip latency may be an indication of a travel time of a message from the wireless mobile device 100 to the wireless head-wearable sensor arrangement (e.g., and back).

Clock Adjustment Based on Synchronization Deviation

In example c), the second processor 208 may be configured to determine the adjustment amount instruction for the first clock to instruct the wireless head-wearable sensor arrangement to adjust the first clock such that the determined synchronization deviation is eliminated, minimized (e.g., falls below a predefined tolerance level such as 1 ms, Sms or 10 ms) or compensated. The second processor 208 may be configured to perform multiple cycles of sending the time information request message and receiving the time information response message, determine the synchronization deviation for each pair of time information request message and time information response message, and determine the adjustment amount instruction for the first clock to instruct the wireless head-wearable sensor arrangement to adjust the first clock such that a smallest of the determined synchronization deviations is eliminated, minimized or compensated or such that an average of the determined synchronization deviations is eliminated, minimized or compensated.

In example d), the second processor 208 may be configured to synchronize the second clock by adjusting the second clock such that the determined synchronization deviation is eliminated, minimized (e.g., falls below a predefined tolerance level such as 1 ms, Sms or 10 ms) or compensated. The second processor 208 may be configured to perform multiple cycles of sending the time information request message and receiving the time information response message, determine the synchronization deviation for each pair of time information request message and time information response message, and adjust the second clock such that a smallest of the determined synchronization deviations is eliminated, minimized or compensated or such that an average of the determined synchronization deviations is eliminated, minimized or compensated.

First Variant of Initiating Time-Synchronization Procedure

In a first variant (e.g., of any one of examples a), b), c) and d)), the second processor 208 may be configured to receive a time synchronization request message from the wireless head-wearable sensor arrangement via the second wireless interface and to start performing the time-synchronization procedure in response to (e.g., responsive to or triggered by) receiving the time synchronization request message. The time synchronization request message may comprise a fourth time-stamp (e.g., generated using the first clock) of a time of sending the time synchronization request message and the second processor 208 may be configured to pre-adjust the second clock based on the time of sending the time synchronization request message as indicated by the fourth time-stamp, before performing the time-synchronization procedure. The second processor 208 may be configured to pre-adjust the second clock if the time indicated by the fourth time-stamp deviates more than a predefined amount (e.g., 1 s, Ss or 10 s) from a time of receiving the time synchronization request message (e.g., determined using the second clock 206).

Second Variant of Initiating Time-Synchronization Procedure

In a second variant (e.g., of any one of examples a), b), c) and d)), the second processor 208 may be configured to send a time synchronization request message to the wireless head-wearable sensor arrangement via the second wireless interface to trigger (e.g., instruct or initiate) the wireless head-wearable sensor arrangement to start performing a time-synchronization procedure. The time synchronization request message may comprise a fourth time-stamp (e.g., generated using the second clock 206) of a time of sending the time synchronization request message and instruct the head-wearable sensor arrangement to pre-adjust the first clock based on the time of sending the time synchronization request message as indicated by the fourth time-stamp, before performing the time-synchronization procedure. The time synchronization request message may instruct the wireless head-wearable sensor arrangement to pre-adjust the first clock if the time indicated by the fourth time-stamp deviates more than a predefined amount (e.g., 1 s, Ss or 10 s) from a time of receiving the time synchronization request message (e.g., determined using the first clock).

Sending Data to the Computing System

The second processor 208 may be configured to send, to the computing system, a fifth time-stamp (e.g., generated using the second clock 206) of a time of sending the medical data. The second processor 208 may be configured to send at least one of an indication of the adjustment amount of the first clock, an indication of the adjustment amount of the second clock 206, the adjustment amount instruction for the first clock and the adjustment amount instruction for the second clock to the computing system. In other words, the second processor 208 may be configured to inform the computing system of a time deviation between the first clock and the second clock compensated in the time-synchronization procedure.

Repeating Time-Synchronization Procedure

The second processor 208 may be configured to repeat the time-synchronization procedure (e.g., at one or more predetermined time points, periodically, after the at least one measurement has been generated or obtained, and/or after the second processor 208 has received the medical data from the wireless head-wearable sensor arrangement). The second processor 208 may be configured to send at least one of an indication of a time amount with which the first clock is adjusted in the repeated (e.g., second or subsequent) time-synchronization procedure, an adjustment amount instruction for the first clock used in the repeated time-synchronization procedure, an indication of a time amount with which the second clock 206 is adjusted in the repeated time-synchronization procedure and an adjustment amount instruction for the second clock 206 used in the repeated time-synchronization procedure to the computing system. The second processor 208 may be configured to send an indication of a time amount with which the first clock is adjusted in the repeated time-synchronization procedure or an indication of a time amount with which the second clock 206 is adjusted in the repeated time-synchronization procedure to the computing system. In other words, the second processor 208 may be configured to inform the computing system (e.g., by sending information to the computing system) about a time deviation between the first clock and the second clock compensated in the repeated time-synchronization procedure.

The second processor 208 may be configured to send an indication of a time-association between the adjustment amount or the adjustment amount instruction and the at least one measurement to the computing system. That is, the second processor 208 may be configured to send an indication of a time-association between a time at which the adjustment amount was used to adjust the first or the second clock and the (e.g., start or end of the) at least one measurement, or send an indication of a time-association between a time at which the adjustment amount instruction was used to adjust the first or the second clock and the (e.g., start or end of the) at least one measurement to the computing system.

Stimulus

The device 200 may further comprise a stimulus interface 210 (e.g., a display or a speaker) configured to provide at least one stimulus to a user of the wireless mobile device. The second processor 208 may be configured to control the stimulus interface 210 to provide the at least one stimulus to the user at one or more stimulus time points at which, optionally, the time synchronization procedure is not performed. In the second variant (e.g., of any one of examples a), b), c) or d)), the second processor 208 may be configured to send the time synchronization request message to the wireless head-wearable sensor arrangement at a time different from the one or more stimulus time points.

The stimulus interface 210) may comprise or be at least one of a (e.g., touch) display, a speaker, an audio output interface connectable to a speaker, haptic vibration interface, an electrostimulation electrode and an odor discharge unit.

Time Misalignment at Start of Measurement

The second processor 208 may be configured to send a sixth time-stamp (e.g., generated using the second clock 206) of a time at which the generation of the at least one measurement is (e.g., instructed to be) started to the computing system.

The at least one time-stamp allocated to the at least one measurement may be indicative of a time provided by the first clock at which the generation of the at least one measurement was started, wherein the sixth time-stamp may be indicative of a time provided by the second clock at which the generation of the at least one measurement was started. That is, a deviation between the time indicated by the at least one time-stamp and the sixth time-stamp may be representative of a time misalignment between the first and the second clock at the time the generation of the at least one measurement was started. The second processor 208 may be configured to send an indication of this time misalignment to the computing system.

Time Misalignment During Measurement

The second processor 208 may be configured to send, to the computing system, a ninth time-stamp (e.g., generated using the second clock 206) of a (e.g. predetermined) time at which the generation of the at least one measurement is ongoing. The at least one time-stamp allocated to the at least one measurement may be indicative of a time provided by the first clock at which the generation of the at least one measurement was ongoing, wherein the ninth time-stamp may be indicative of a time provided by the second clock at which the generation of the at least one measurement was ongoing. That is, a deviation between the time indicated by the at least one time-stamp and the ninth time-stamp may be representative of a time misalignment between the first and the second clock at the time the generation of the at least one measurement was ongoing. The second processor 208 may be configured to send an indication of this time misalignment to the computing system.

Time Misalignment at End of Measurement

The at least one time-stamp allocated to the at least one measurement may be indicative of a time provided by the first clock at which the generation of the at least one measurement was finished. The second processor 208 may be configured to send a seventh time-stamp (e.g., generated using the second clock 206) of a time at which the medical data was received by the device 200 to the computing system.

The seventh time-stamp may be corrected by the second processor 208 (e.g., based on the round-trip latency) to obtain a theoretical time, as provided by the second clock, at which the medical data was sent by the arrangement to the device. The second processor 208 may be configured to send, to the computing system, the seventh timestamp and/or an eighth time-stamp indicating the theoretical time. That is, a deviation between the time indicated by the at least one time-stamp and the seventh or eighth time-stamp may be representative of a time misalignment between the first and the second clock at the time the generation of the at least one measurement was finished. The second processor 208 may be configured to send an indication of this time misalignment to the computing system.

Stimulus and Start Message

The second processor 208 may be configured to send a start message to the wireless head-wearable sensor arrangement instructing the wireless head-wearable sensor arrangement to start generating the at least one measurement in response to receiving the start message or at a time specified by the start message. The second processor 208 may be configured to determine the time specified by the start message and/or to send the start message at a point in time such that the at least one measurement is generated at least during the one or more stimulus time points.

Alternatively, the second processor 208 may be configured to start providing the at least one stimulus in response to receiving a start message from the wireless head-wearable sensor arrangement.

The start message may correspond to the configuration message.

The second processor 208 may be configured to send an indication of the one or more stimulus time points to the computing system. The indication of the one or more stimulus time points may comprise a time-association between the one or more stimulus time points and the at least one measurement.

The at least one stimulus may comprise one or more of a visual, an auditory, a haptic and an olfactory stimulus. The at least one stimulus may evoke a response in the biosignal. The at least one stimulus may trigger a body response of the user observable or represented in the biosignal. The at least one stimulus may have an effect on the user such that the biosignal exhibits at least one (e.g., characteristic) feature associated with the at least one stimulus.

User Interface

The device 200 may further comprise a user interface 212 configured to receive a user input. The second processor 208 may further be configured to transmit, to the computing system, user data describing the user input. The user data may comprise a time-association between one or more time points of received user input and the at least one measurement. The user interface 212 may comprise at least one of a touch screen (e.g., also used as the stimulus interface 210), a computer mouse, a joystick and a microphone.

Type of Wireless Device and Arrangement Sent to Computing System

The second processor 208 of the device of the second aspect may be configured to send an indication of a type (e.g., at least one of a device name, a manufacturer name, a model number and a version number) of the device 200 or the wireless head-wearable sensor arrangement to the computing system. The computing system described herein with reference to FIG. 2 may be the computing system as discussed below with reference to FIG. 3.

Computing System

Figure 3:
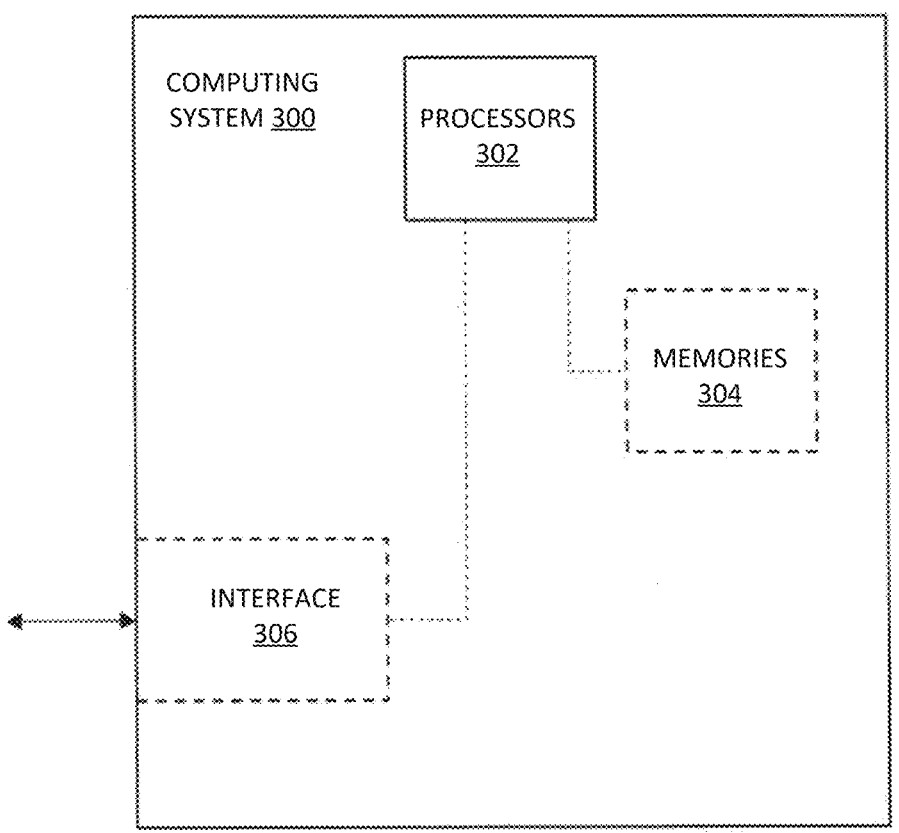
FIG. 3 shows an embodiment of a computing system in accordance with the present disclosure.

FIG. 3 shows a first embodiment of a computing system 300 in accordance with the present disclosure. The computing system 300 comprises one or more processors 302 and may comprise one or more memories 304. The one or more memories 304 may comprise instructions which, when performed by the one or more processors 302, configure the processors as described herein. The computing system 300 may comprise an interface 306 for receiving and sending data.

The one or more processors 302 are configured to receive, from a wireless mobile device, medical data comprising a representation of at least one measurement of a biosignal of a user wearing a wireless head-wearable sensor arrangement and at least one time-stamp (e.g., that has been) allocated to the at least one measurement. The at least one time-stamp may have been allocated to the at least one measurement by the wireless head-wearable sensor arrangement, for example using a first clock of the wireless head-wearable sensor arrangement. The one or more processors may be configured to determine, based on the representation of the at least one measurement and the at least one time-stamp allocated to the at least one measurement, an indicator of health, well-being or performance of the user of the wireless head-wearable sensor arrangement. The wireless head-wearable sensor arrangement may be the arrangement 100. The wireless mobile device may be the device 200. The medical data received by the one or more processors 302 may be the medical data sent by the device 200 as described with reference to FIG. 2.

The computing system 300 may be a cloud-based processing system. The one or more processors 302 may be distributed across different racks or geographical locations. The one or more processors 302 may be implemented as virtual resources (VRs) of a virtual machine (VM). The computing system 300 may be configured to receive the medical data from the wireless mobile device via a network such as the internet.

The representation of the at least one measurement may correspond to, consist of or comprise the at least one measurement. The representation of the at least one measurement may comprise or consist of a digitized or numerical conversion of the at least one measurement, or a (e.g., frequency-, amplitude- and/or noise-) filtered version of the at least one measurement.

The at least one time-stamp may have been allocated to the at least one measurement (e.g., by the wireless head-wearable sensor arrangement) using the first clock (e.g., the first clock 106) running synchronous with a second clock (e.g., the second clock 206) of the wireless mobile device (e.g., at least at a start of obtaining the at least one measurement by at least one sensor (e.g., the at least one sensor 102) comprised in the wireless head-wearable sensor arrangement). As noted above, the term "running synchronous" as used herein means that a time misalignment or difference between a time provided by the first clock and a time provided by the second clock at the same point in time is below a predefined tolerance level such as 1 ms, Sms or 10 ms or is essentially zero (e.g., is below a predefined tolerance level such as 0.1 ms, 0.Sms or 1 ms).

Packet Numbers

The received medical data may be divided into a plurality of data packets (e.g., by the wireless head-wearable sensor arrangement or the wireless mobile device), and a packet number may be assigned to each data packet. The packet number may indicate a relative position of the packet in the medical data or the at least one measurement. Each data packet may comprise a part of the at least one measurement and the packet number may indicate which part of the at least one measurement is included in the packet. The data packets may be separately received by the computing system 300 from the wireless mobile device 200. The data packets may, after being received by the computing system 300, be re-ordered by the one or more processors 302 based on the packet numbers to obtain the medical data in the correct form. That is, the one or more processors 302 may re-order the received data packets such that the order complies with the packet numbers. This may ensure that the parts of the at least one measurement comprised in the packets are joined in the correct sequence.

Time Misalignment at Start of Measurement

The one or more processors 302 may be configured to receive, from the wireless mobile device, a sixth time-stamp (e.g., generated using the second clock) of a time at which a generation of the at least one measurement by at least one sensor of the wireless head-wearable sensor arrangement is (e.g., instructed to be) started to the computing system. The at least one time-stamp allocated to the at least one measurement may be indicative of a time provided by the first clock at which the generation of the at least one measurement was started, wherein the sixth time-stamp may be indicative of a time provided by the second clock at which the generation of the at least one measurement was started. That is, a deviation between the time indicated by the at least one time-stamp and the sixth time-stamp may be representative of a time misalignment between the first and the second clock at the time the generation of the at least one measurement was started. The one or more processors 302 may be configured to receive, from the wireless mobile device, an indication of this time misalignment.

Time Misalignment During Measurement

The one or more processors 302 may be configured to receive, from the wireless mobile device, a ninth time-stamp (e.g., generated using the second clock 206) of a (e.g. predetermined) time at which the generation of the at least one measurement was ongoing. The at least one time-stamp allocated to the at least one measurement may be indicative of a time provided by the first clock at which the generation of the at least one measurement was ongoing, wherein the ninth time-stamp may be indicative of a (e.g., corresponding) time provided by the second clock at which the generation of the at least one measurement was ongoing. That is, a deviation between the time indicated by the at least one time-stamp and the ninth time-stamp may be representative of a time misalignment between the first and the second clock at the (e.g., predetermined) time the generation of the at least one measurement was ongoing. The one or more processors 302 may be configured to receive an indication of this time misalignment from the wireless mobile device.

Time Misalignment at End of Measurement

The at least one time-stamp allocated to the at least one measurement may be indicative of a time provided by the first clock at which the generation of the at least one measurement was finished. The one or more processors 302 may be configured to receive, from the wireless mobile device, a seventh time-stamp (e.g., generated using the second clock 206) of a time at which the medical data was received by the wireless mobile device. The seventh time-stamp may be corrected by wireless mobile device (e.g., based on the round-trip latency) to obtain a theoretical time, as provided by the second clock, at which the medical data was sent by the wireless head-wearable sensor arrangement to the wireless mobile device. The one or more processors 302 may be configured to receive, from the wireless mobile device, the seventh and/or an eighth time-stamp indicating the theoretical time. That is, a deviation between the time indicated by the at least one time-stamp and the seventh or eighth time-stamp may be representative of a time misalignment between the first and the second clock at the time the generation of the at least one measurement was finished. The one or more processors 302 may be configured to receive an indication of this time misalignment from the wireless mobile device.

Determine Indicator

Based on the representation of the at least one measurement and the at least one time-stamp allocated to the at least one measurement, an indicator of health, well-being or performance of the user may be determined. The one or more processors 302 may be configured to use the at least one time-stamp for identifying a temporal property (e.g., a frequency of a characteristic pattern, a shape of the representation in the time domain or the like) of the representation of the at least one measurement. The temporal property may be a feature associated with one of a predefined set of indicators of health, well-being or performance of the user. The one or more processors 302 may be configured to select the one of the set of indicators based on the temporal property.

The one or more processors may be configured to receive, from the wireless mobile device, a fifth time-stamp (e.g., generated by the first clock) of a time of sending the medical data, and determine the indicator of health, well-being or performance of the user further based on the fifth time-stamp.

Use Indication on Adjustment Amount

The one or more processors 302 may be configured to receive, from the wireless mobile device (e.g., the wireless mobile device 200), an indication of an adjustment amount of either the first clock or the second clock used (e.g., by the wireless device and/or the wireless head-wearable sensor arrangement, for example before or after the at least one measurement has been obtained) for synchronizing the first clock or the second clock. The adjustment amount may have been determined or received by the wireless mobile device 200 in the (e.g., initial or first) time synchronization procedure or the repeated (e.g., second or subsequent) time synchronization procedure described above with reference to FIGS. 1 and 2. Alternatively or additionally, the one or more processors 302 may be configured to receive, from the wireless mobile device, an adjustment amount instruction used (e.g., by the wireless device and/or the wireless head-wearable sensor arrangement, for example before or after the at least one measurement has been obtained) for synchro-nizing the first clock or the second clock. The adjustment amount instruction may have been determined or received by the wireless mobile device 200 in the (e.g., initial or first) time synchronization procedure or the repeated (e.g., second or subsequent) time synchronization procedure described above with reference to FIGS. 1 and 2. The one or more processors 302 may be configured to determine the indicator of health, well-being or performance of the user further based on the indication of the adjustment amount or the adjustment amount instruction.

Use Time-Association Between Adjustment Amount and Measurement

The one or more processors 302 may be configured to receive a time-association between the adjustment amount and the at least one measurement or the adjustment amount instruction and the at least one measurement from the wireless mobile device, wherein the one or more processors 302 may be configured to determine the indicator of health, well-being or performance of the user further based on the time-association. This time-association may be a time-asso-ciation between the at least one time-stamp and a time point at which the adjustment amount was used for synchronizing the first clock or the second clock, or a time-association between the at least one time-stamp and a time point at which the adjustment amount instruction was used for synchronizing the first clock or the second clock.

Clock Drift

The one or more processors 302 may be configured to determine a clock drift between the first clock and the second clock based on the adjustment amount, and based on a time-association between the at least one time-stamp and a time point at which the adjustment amount was used for synchronizing the first clock or the second clock (e.g., in the repeated time-synchronization procedure as described above). The one or more processors 302 may be configured to determine a clock drift between the first clock and the second clock based on the received adjustment amount instruction, and based on a time-association between the at least one time-stamp and a time point at which the adjustment amount instruction was used for synchronizing the first clock or the second clock (e.g., in the repeated time-synchronization procedure as described above).

For example, the at least one time-stamp may indicate a time at which the wireless head-wearable sensor arrange-ment started generating the at least one measurement, and the first or second clock was adjusted with a certain adjust-ment amount in the repeated time-synchronization proce-dure described above after or during the at least one mea-surement was generated. In this example, the clock drift (e.g., temporal change of difference between times provided by the first clock and the second clock) may be determined as the certain adjustment amount per time period, wherein the time period corresponds to the time-association (e.g., relative time difference) between the time indicated by the at least one time-stamp and the time the first or second clock was adjusted with the certain adjustment amount. The one or more processors 302 may be configured to determine the indicator of health, well-being or performance of the user further based on the clock drift.

Use of Stimulus Time Points

The one or more processors 302 may be configured to receive, from the wireless mobile device, an indication of one or more stimulus time points at which at least one stimulus is provided to the user, and determine the indicator of health, well-being or performance of the user further based on the indication of the one or more stimulus time points.

The indication of the one or more stimulus time points may comprise a time-association between the one or more stimulus time points and the at least one measurement and/or the at least one time-stamp. The indication of the one or more stimulus time points may be used to segment the (e.g., representation of the) at least one measurement into a plurality of segments. Each of the segments may correspond to an epoch of the biosignal. Each segment may be identified as a predefined time slot with reference to one or more of the stimulus time points. For example, each segment may be a time slot starting S0 ms before a stimulus time point and ending 450 ms after the stimulus time point. The one or more processors 302 may be configured to analyze the plurality of segments to identify features present in a predefined number, most or all of the segments. The indicator of health, well-being or performance of the user may be determined based on the identified features.

Use of User Data

The one or more processors 302 may be configured to receive, from the wireless mobile device, user data describ-ing a user input received via a user interface of the wireless mobile device, wherein the one or more processors 302 may be configured to determine the indicator of health, well-being or performance of the user further based on the user data.

The user data may comprise a time-association between one or more time points of received user input and the at least one measurement. The user data may comprise a time-association between the one or more time points of received user input and the one or more stimulus time points. The user data may comprise a selection of a predefined set of alternatives, for example provided to the user via the user interface or the stimulus interface. The one or more proces-sors may be configured to determine the indicator of health, well-being or performance of the user based on the identified features and the user data. For instance, the type or properties of (e.g., the) features to be identified by the one or more processors 302 may be selected from a predefined set of types or properties by the one or more processors 302 based on the user data.

Use of Indication of Type of Wireless Device or Arrangement

The one or more processors 302 may be configured to receive, from the wireless mobile device, an indication of a type of the wireless mobile device or the wireless head-wearable sensor arrangement, obtain predefined information on a time delay associated with the type of the wireless mobile device or the wireless head-wearable sensor arrangement, and determine the indicator of health, well-being or performance of the user further based on the time delay.

The predefined information on the time delay may be information on a time delay between a stimulus time point provided by a processor of the wireless mobile device and a real time point at which the stimulus is output. The one or more processors 302 may be configured to adjust the one or more stimulus time points as defined by the received indication of the one or more stimulus time points based on the predefined information on the time delay. For example, the indication of the type of the wireless device may specify that the wireless device is manufactured by a certain company, such as Samsung®. The predefined information on the time delay may specify that the one or more stimulus time points as provided by the Samsung® wireless device in the indication are in fact 30 ms sooner than the real time points at which the stimulus is output via the stimulus interface (e.g., a visual stimulus output on the display, an auditory stimulus output via the speaker or audio output interface, or a tactile stimulus output via the haptic vibration interface). The one or more processors 302 may thus time-adjust the one or more stimulus time points as defined in the received indication on the one or more stimulus time points (e.g., in the above example of the Samsung® wireless device, by adding 30 ms to each of the one or more stimulus time points).

A time-association between the one or more stimulus time points and the at least one measurement may be changed based on the predefined information on the time delay. The one or more processors 302 may then use the time-adjusted one or more stimulus time points as described above for the (e.g., non-adjusted) one or more stimulus time points.

Wireless mobile devices of different types may introduce different delays between a user response and that response being registered by the wireless mobile device via the user interface (for example user input received via a microphone, touch screen, or accelerometer). The one or more processors 302 may be configured to adjust, based on the predefined information on the time delay, the one or more time points of received user input and/or the time-association between the one or more time points of received user input and the at least one measurement.

Adjust Measurement

The one or more processors 302 may be configured to determine at least one time-adjusted measurement by adjusting at least a part of the representation of the at least one measurement in time based on at least some of the information received from the wireless mobile device and determine the indicator of health, well-being or performance of the user of the wireless head-wearable sensor arrangement based on the at least one time-adjusted measurement. In other words, the representation may be stretched, squeezed or scaled (e.g., in a time domain) based on at least some of the information received from the wireless mobile device, for example based on the indication on the one or more stimulus time points, the indication on the adjustment amount or the adjustment amount instruction. The at least a part of the at least one measurement may be adjusted in time by scaling it such that the at least one time-stamp corresponds to or complies with the one or more stimulus time points. The at least a part of the at least one measurement may be adjusted (e.g., linearly scaled) in time to compensate for the clock drift between the first clock and the second clock determined as described above. In this context it is noted that the clock drift to be compensated may be assumed to be constant, one or more stimulus time points may be defined using the second clock, whereas the at least one measurement may be time-stamped with the at least one time-stamp defined using the first clock.

Adjust Time-Stamp

The one or more processors 302 may be configured to determine at least one time-adjusted time-stamp by adjusting the at least one time-stamp allocated to the at least one measurement in time based on (e.g., all of, or at least some of) the information received from the wireless mobile device (e.g., based on one or more of the adjustment amount, the adjustment amount instruction, the time misalignment, the at least one timestamp, the sixth timestamp, the seventh timestamp, the eighth timestamp and the ninth timestamp), and determine the indicator of health, well-being or performance of the user of the wireless head-wearable sensor arrangement further based on the at least one time-adjusted time-stamp. The at least one time-stamp may be adjusted based on the predefined information on the time delay as described above. The at least one time-stamp may be adjusted such that it has a predefined relative temporal position with respect to one or more of the stimulus time points. By adjusting the at least one time-stamp, the portions of the representation of the at least one measurement associated with the at least one timestamp may be scaled.

Adjust Time-Association of Stimulus Time Points

The one or more processors 302 may be configured to determine time-adjusted stimulus data by adjusting the time-association between the one or more stimulus time points and (e.g., the at least one time-stamp allocated to) the at least one measurement based on at least some of the information received from the wireless mobile device (e.g., one or more of the time misalignment, the adjustment amount, the adjustment amount instruction, the time-association between the adjustment amount and the at least one measurement, or the adjustment amount instruction and the at least one measurement), and determine the indicator of health, well-being or performance of the user of the wireless head-wearable sensor arrangement further based on the time-adjusted stimulus data. The time-association between the one or more stimulus time points and the at least one measurement may be (e.g., linearly) adjusted to compensate for the (e.g., constant) clock drift between the first clock and the second clock determined as described above.

Adjust Time-Association of User Input Time Points

The one or more processors 302 may be configured to determine time-adjusted user data by adjusting the time-association between the one or more time points of received user input and the at least one measurement based on at least some of the information received from the wireless mobile device (e.g., one or more of the time misalignment, the adjustment amount, the adjustment amount instruction, the time-association between the adjustment amount and the at least one measurement, or the adjustment amount instruction and the at least one measurement), and determine the indicator of health, well-being or performance of the user of the wireless head-wearable sensor arrangement further based on the time-adjusted user data. The time-association between the one or more time points of received user input and the at least one measurement may be adjusted to compensate for the (e.g., constant) clock drift between the first clock and the second clock determined as described above. In this context it is noted that the one or more time points of received user input may be defined using the second clock, whereas the at least one measurement may be time-stamped with the at least one time-stamp defined using the first clock.

Feature Identification

The one or more processors 302 may be configured to identify, based on at least some of the information received from the wireless mobile device (e.g., the medical data, the time misalignment, the indication on the adjustment amount, the adjustment amount instruction, the indication on the type of the wireless device or the wireless head-wearable sensor arrangement, the indication on the one or more stimulus time points and/or the user data), in the at least one measurement and/or the at least one time-corrected (e.g., time-adjusted or scaled) measurement, at least one feature indicative of a state of the user's brain health, and to determine the indicator of health, well-being or performance of the user of the wireless head-wearable sensor arrangement based on the identified at least one feature.

The at least one feature indicative of the state of the user's brain health may be the feature described above having predetermined (e.g., spatial, temporal and/or frequency) properties.

The one or more processors 302 may be configured to identify the at least one feature indicative of the state of the user's brain health using a machine-learning based classifier and/or to determine the indicator of health, well-being or performance of the user based on the identified at least one feature using a machine-learning based classifier. Examples of such machine-learning based classifiers include logistic regression, random forests and other tree-based methods, support vector machines, (deep) neural networks and their variants.

The one or more processors 302 may be configured to identify the at least one feature using at least one of frequency analysis and connectivity analysis, such as power spectral density estimates, event-related spectral perturbations, granger causality, inter-trial phase coherence, phase-locking values, low-resolution electrical tomography or its variants, beamforming, brain-electrical source analysis, etc.

In case the biosignal is an EEG signal, the at least one feature may comprise at least one of evoked potentials, EPs, and event related potentials, ERPs, spectral measures such as event-related spectral perturbations, power spectral density, measures of connectivity, and measures of complexity and entropy.

Visual Output of Processing Result

The one or more processors 302 may be configured to determine a visual representation of the indicator of health, well-being or performance of the user and output the visual representation to a display (e.g., to a display of a user terminal connected to the computing system 300, to the stimulus interface of the wireless device 200 or to the user input interface of the wireless device 200).

Processing System

FIG. 4 shows an embodiment of a medical data processing system 1000 in accordance with the present disclosure. The medical data processing system 1000 may comprise the wireless head-wearable sensor arrangement 100, the wireless mobile device 200, and the computing system 300. The first wireless interface 104 of wireless head-wearable sensor arrangement 100 may be communicatively coupled to the second wireless interface 204 of the wireless mobile device 200. The wireless mobile device 200 may be communicatively coupled to the computing system 300, for example via a wired or wireless connection (e.g., via the second wireless interface 204).

First Medical Data Processing Method

FIG. 5 shows an embodiment of a first medical data processing method in accordance with the present disclosure.

The method is a medical data processing method for obtaining a processed measurement of a biosignal from an initial measurement of the biosignal. The method is performed by a computing system (e.g., the computing system 300). The method comprises a step 500 of obtaining medical data describing at least one initial measurement (e.g., the at least one measurement described above) of a biosignal in a first domain. The method comprises a step 502 of decomposing the at least one initial measurement into a joint frequency domain to obtain transformed data representing the at least one initial measurement in both the first domain and the frequency domain. The method comprises a step 504 of fitting at least one autoregressive model to the transformed data. The method comprises a step 506 of determining at least one deviation between the at least one fitted autoregressive model and the transformed data. The method comprises a step 508 of obtaining a processed measurement of the biosignal based on the at least one deviation.

Processed Data

The processed measurement is referred to as "processed", as it is determined by the computing system based on the at least one initial measurement and can be regarded as being a result of processing the initial measurement by the computing system. The processed measurement may be an enhanced measurement. The processed measurement may have an improved signal-to-noise ratio relative to the initial measurement. The biosignal may comprise a plurality of epochs, wherein the processed measurement of the biosignal may have a lower standard deviation across the epochs compared with the initial measurement.

The processed measurement may be enhanced such that characteristic features can be identified more reliably therein (e.g., using a machine-learning based classifier), an amplitude of artefacts is reduced therein and/or a number of artefacts is reduced therein. The characteristic features may be indicative of health, well-being or performance of a human or animal the body of which provides the biosignal.

Medical Data

The medical data may be obtained from a wireless mobile device (e.g., the wireless mobile device 200) as described herein. The medical data may describe the at least one initial measurement by comprising the at least one initial measurement, 35 comprising a (e.g., numerical or digital) representation of the at least one initial measurement, or comprising a (e.g., highpass-, bandpass- or lowpass-) filtered version of the at least one initial measurement.

Transformed Data

The term "transformed data" may relate to the fact that the data represents a "transformed" (e.g., decomposed) version of the at least one initial measurement.

The transformed data may comprise or consist of a decomposed version of the at least one initial measurement. The decomposed version of the at least one initial measurement may represent the at least one measurement in the joint domain. The transformed data may comprise a representation of the at least one initial measurement in the joint domain. The transformed data may comprise a representation of the at least one initial measurement in the joint domain. The transformed data may comprise a representation of the at least one initial measurement in the joint domain. The transformed data may comprise a representation of the at least one initial measurement in both the first domain and the frequency domain.

Autoregressive Model

The at least one (e.g., two or more) autoregressive model may be an autoregressive model AR(p) of order p, wherein p may be equal to 1 or more. In another example, p may be 2 or 3. The at least one autoregressive model may be fitted to the transformed data (e.g., the representation of the at least one initial measurement in both the first domain and the frequency domain) such that an error measurement, e.g. a maximum, average or mean deviation, between the at least one autoregressive model and the transformed data is minimized. The at least one autoregressive model may be fitted to the transformed data by estimating or adapting one or more parameters of the at least one autoregressive model. The one or more parameters may be estimated based on a least squares procedure or a method of moments based on the Yule-Walker equations. Other possibilities of fitting an AR model to data may be known to those skilled in the art and applied here. One way of fitting an autoregressive model to a segment comprised in the transformed data will be described further below.

Obtaining the processed measurement may comprise using the at least one deviation as the processed measurement or determining the processed measurement based on the at least one deviation. The at least one deviation may be determined in the joint domain.

Recomposition and Invertible Transformation

Determining the processed measurement may comprise recomposing the at least one deviation into the first domain. The recomposing of the at least one deviation may transform the at least one deviation from the joint domain into the first domain.

The at least one initial measurement may be decomposed into the joint frequency domain by applying an invertible transform, e.g. a bijective function. The at least one deviation may be recomposed into the first domain by applying an inverse of the invertible transform. An interpolation or approximation function may be fitted to the at least one deviation across the first domain, and the fitted function may be recomposed into the (e.g., original, pre-decomposition or singular) first domain to obtain the processed measurement.

Residuals

The at least one deviation may comprise or consist of one or more residuals of the at least one fitted autoregressive model. The at least one deviation may comprise all residuals of the at least one fitted autoregressive model. The commonly known definition of the term "residual" shall apply, which is consistently used in the area of autoregressive models. Alternatively or additionally, a residual may be a deviation between the fitted autoregressive model and the data to which it is fitted.

Decomposition Sequences

The at least one initial measurement (e.g., corresponding to the at least one measurement described above) may be decomposed into the joint frequency domain to determine, for each of a plurality of frequencies or frequency bands and each of the at least one initial measurement, a separate decomposition sequence, the transformed data comprising the determined decomposition sequences. Each decomposition sequence may define a part of the at least one initial measurement in a predefined frequency or frequency band. The at least one initial measurement may be decomposed into a plurality of decomposition sequences, each decomposition sequence associated with a different frequency or frequency band. Each decomposition sequence may describe a (e.g., frequency-) decomposed part of the at least one initial measurement in the first domain. Each of the decomposition sequences may have an amplitude that corresponds to a magnitude of coefficients obtained by a transformation used for the decomposition of the at least one initial measurement.

Fit Autoregressive Model to Segment

The at least one autoregressive model may be fitted to the transformed data across or in the first domain. The at least one autoregressive model may be fitted to at least one segment of one of the decomposition sequences (e.g., across the first domain of the at least one segment).

The at least one autoregressive model may be a vector autoregressive model, VAR, and may be fitted to (e.g., a plurality of segments of) one or more of the decomposition sequences. The VAR model may be fitted to all segments comprising a predefined point in the first domain or adjacent to a predefined point in the first domain. The predefined point may be a (e.g., time or location) point in the first domain at which a stimulus is provided to the human or animal, the stimulus evoking (e.g., a response in) the biosignal. The fitted VAR model may comprise a parameter adaptable to a signal type such that, by adapting the parameter, the fitted VAR model is fitted to a signal type of interest. Different signal types may be representative of different features (e.g., representing a state of brain health). The parameter may be an exogenous factor denoting additional information about the stimulus, e.g. a type of stimulus, a stimulus intensity, or a stimulus point in time or space. In this case, the AR model may be an Autoregressive Linear Mixed Effects Model.

The at least one autoregressive model may be fitted to at least one segment of two or more different decomposition sequences for a same frequency or frequency band.

The at least one segment may be defined as an interval in the first domain. The interval may have a predefined length. The predefined length may be longer than a length of a feature of interest to be identified in the processed measurement.

The at least one segment may correspond to a single epoch of the biosignal. An epoch may be a segment of data that is expected (e.g., due to a stimulus provided, an instruction, or other occurrence affecting and precisely time-locked with the biosignal) to correspond to or comprise a feature of interest recorded in the biosignal. The epoch may be a part of the biosignal comprising at least one feature of interest. The epoch may be referred to as a trial. The epoch may be a time window having a predefined length. The predefined length may be longer than a length of a feature of interest to be identified in the processed measurement.

Identify Segment

The method may further comprise identifying (e.g., defining) the at least one segment in the at least one initial measurement or in the one, two or more decomposition sequences.

The at least one segment may be defined with respect to a first point in the first domain (e.g., a stimulus point), the first point being associated with a stimulus evoking or influencing the biosignal. The first point may be a point in time referred to as stimulus time point herein.

Alternatively, the at least one segment may be identified by matching a first point in the first domain (e.g., a stimulus point), the first point associated with a stimulus evoking or influencing the biosignal, to a second point (e.g., in the first domain) in the at least one initial measurement or the one, two or more decomposition sequences. The matching may be based on a first-domain-association between the first point and the and at least one initial measurement or based on a first-domain-association between the first point and the one, two or more decomposition sequences. The first point may correspond to the second point in the first domain. The at least one segment may be defined with respect to the second point.

The method may comprise obtaining an indication of the first point, for example from a wireless mobile device such as the wireless mobile device 200.

The method may comprise obtaining an indication of one or more stimulus time points comprising a time-association between the one or more stimulus time points and the at least one initial measurement. A relative position of the stimulus time points with respect to the at least one initial measurement may be determined based on the time-association between the one or more stimulus time points and the at least one initial measurement. The relative position may be used to segment the (e.g., representation of the) at least one initial measurement into the segments. Each segment may be identified as a predefined time slot with reference to one or more of the stimulus time points. For example, each segment may be a time slot starting a first predefined time amount (e.g., SOms) before a stimulus time point and ending a second predefined time amount (e.g., 450 ms) after the stimulus time point.

The stimulus may be at least one of an auditory, a visual, a haptic or an olfactory stimulus provided to a human or animal, the body of which provides the biosignal.

Segment Decomposition

Each of the at least one identified segment of the at least one initial measurement may be individually decomposed into the joint frequency domain to obtain the at least one segment of the one, two or more decomposition sequences.

Overlapping Initial Measurement

The at least one initial measurement may comprise a first initial measurement of the biosignal in a first section of the first domain and a second initial measurement of the biosignal in the first section of the first domain. The first initial measurement may overlap the second initial measurement in the first domain. For example, multiple measurements may have been performed at a same time, resulting in the first and second initial measurement of the biosignal in the time domain.

(Wavelet) Transformation

The at least one initial measurement may be decomposed into the joint frequency domain by applying a transform having a varying resolution in the first domain (e.g., a varying first-domain resolution). The varying resolution may vary across frequencies. The at least one initial measurement may be decomposed into the joint frequency domain by applying a wavelet-based transform. The wavelet-based transform may be a Discrete Wavelet Transform, DWT. The wavelet-based transform may for example use a wavelet from the Debauchies-4, Symlet-5 or Coiflet-2 mother wavelet family. Further wavelet forms are or may become apparent to the skilled person working in the field of wavelet transformation. Each of the decomposition sequences may have an amplitude that corresponds to a magnitude of approximation or detail coefficients obtained by the DWT.

First Domain and Joint Frequency Domain

The joint frequency domain may be a joint (e.g., combined) domain of the first domain and the frequency domain. In a first variant, the first domain may be a time domain, the joint frequency domain may be a time-frequency domain and the at least one initial measurement may optionally be a time-variable measured amplitude. In a second variant, the first domain may be a spatial domain, the joint frequency domain may be a space-frequency domain and the at least one initial measurement may optionally be a space-variable measured amplitude.

Computing System and Computer Program Product for First Medical Data Processing Method The present disclosure also provides for a computing system comprising at least one memory and at least one processor, the at least one memory storing instructions which, when executed on the at least one processor, cause the at least one processor to carry out the method according to the fifth aspect. The computing system may be the system 300 described herein, wherein the at least one processor corresponds to the one or more processors 302, and the at least one memory corresponds to the one or more memories 304.

The present disclosure also provides for a computer program product comprising program code portions for performing the first medical data processing method when the computer program product is executed on at least one processor (e.g., the one or more processors 302). The computer program product may be stored on one or more computer readable recording media (e.g., the one or more memories 304).

Second Medical Data Processing Method

FIG. 6 shows an embodiment of a second medical data processing method in accordance with the present disclosure.

The second medical data processing method is a medical data processing method for obtaining a processed measurement of a biosignal from an initial measurement of the biosignal. The method is performed by a computing system (e.g., the computing system 300). The method comprises a step 600 of obtaining medical data describing at least one initial measurement (e.g., the at least one measurement described above) of a biosignal in a first domain. The method comprises a step 602 of decomposing the at least one initial measurement into a joint frequency domain to determine, for each of a plurality of frequencies or frequency bands and each of the at least one initial measurement, a separate decomposition sequence in the first domain. The method comprises a step 604 of determining at least one estimation point by applying a robust aggregation method to a plurality of corresponding points in one or more of the decomposition sequences for a same frequency or frequency band. The method comprises a step 606 of recomposing the at least one estimation point into the first domain to obtain a processed measurement of the biosignal.

Processed Data

The processed measurement is referred to as "processed", as it is determined by the computing system based on the at least one initial measurement and can be regarded as being a result of processing the initial measurement by the computing system. The processed measurement may be an enhanced measurement. The processed measurement may have an improved signal-to-noise ratio relative to the initial measurement. The biosignal may comprise a plurality of epochs, wherein the processed measurement of the biosignal has a lower standard deviation across the epochs compared with the initial measurement. The processed measurement may be enhanced such that characteristic features can be identified more reliably therein (e.g., using a machine-learning based classifier), an amplitude of artefacts is reduced therein and/or a number of artefacts is reduced therein. The characteristic features may be indicative of health, well-being or performance of a human or animal the body of which provides the biosignal.

Medical Data

The medical data may be obtained from a wireless mobile device (e.g., the wireless mobile device 200) as described herein. The medical data may describe the at least one initial measurement by comprising the at least one initial measurement, comprising a (e.g., numerical or digital) representation of the at least one initial measurement, or comprising a (e.g., highpass-, bandpass- or lowpass-) filtered version of the at least one initial measurement.

Decomposition Sequence

Each decomposition sequence may define a part of the at least one initial measurement in a predefined frequency or frequency band. The at least one initial measurement may be decomposed into a plurality of decomposition sequences, each decomposition sequence associated with a different frequency or frequency band. Each decomposition sequence may describe a (e.g., frequency-) decomposed part of the at least one initial measurement in the first domain. Each decomposition sequence may have an amplitude that corresponds to a magnitude of coefficients obtained by a transformation used for the decomposition of the at least one initial measurement.

Estimation Point

The at least one estimation point may be an output or result of the robust aggregation method. The at least one estimation point may be determined in the joint domain. The at least one estimation point may be recomposed from the joint domain into the original or pre-decomposition domain. An interpolation or approximation function may be fitted to the at least one estimation point across the first domain, and the fitted function may be recomposed into the (e.g., original, pre-decomposition or singular) first domain to obtain the recomposed at least one estimation point. The at least one estimation point may have a value determined by the robust aggregation method from amplitudes of the decomposed measurement at the corresponding points. The at least one estimation point is referred to as an estimation "point", as it may have a (e.g., pre-) defined position in the first domain.

Applying Robust Aggregation Method

Applying the robust aggregation method to the plurality of corresponding points may comprise applying the robust aggregation method to amplitude values of the plurality of corresponding points expressed in the joint domain. Applying the robust aggregation method may comprise aggregating the amplitude values of the plurality of corresponding points. Applying the robust aggregation method may consist of or comprise determining a statistical measure or value representing a parameter of an assumed (e.g., predefined) underlying distribution (e.g., a Normal distribution or Gamma distribution) or distribution family (e.g. symmetric distributions, bimodal distributions or heavy-tailed distributions) of (e.g., amplitude values of) the plurality of corresponding points.

Robust Aggregation Method

The robust aggregation method may be a robust statistical method for obtaining a measure of an assumed underlying distribution of (e.g., amplitude values of) the plurality of corresponding points. Such measures of the assumed underlying distribution may comprise values of parameters of the assumed underlying distribution such as location, spread, or skewness. The robust aggregation method may provide the measure (e.g., even or only) for data that does not conform to the assumed underlying distribution. The robust aggregation method may be resistant to outliers and/or incorrect assumptions of the distribution. The robust aggregation method may fulfil at least one of the following criteria:
   (i) it is a robust, insensitive and/or resistant statistical method;
   (ii) it has a bounded influence function;
   (iii) it has a breakdown point of 0.5 or a breakdown point between 0.4 and 0.5.
   Applying the robust aggregation method may comprise or consist of estimating a value of a parameter of the assumed underlying distribution using weights applied to the plurality of corresponding points. This weighting may including a-weighting (e.g., to create subsets of data). Applying the robust aggregation method may comprise or consist of determining at least one of a median, a trimmed mean or an M-estimator of the plurality of corresponding points. The trimmed mean may be referred to as truncated mean. The trimmed mean may be an interquartile mean. The at least one estimation point may have a (e.g., amplitude) value corresponding to the parameter of the assumed underlying distribution, such as the median, the trimmed mean or the M-estimator of the corresponding points.

The assumed underlying distribution may be predefined or selected from a set of distributions based on a type of the biosignal and/or based on a feature of interest within the biosignal.

Corresponding Points and Segments

Each of the corresponding points may have a (e.g., first-domain) position similar (e.g., "corresponding") to that of the estimation point. Each of the plurality of corresponding points may have a same or similar position within a segment of the decomposition sequence comprising the corresponding point. The same position may be a first-domain position. Each segment of the determined decomposition sequences may comprise only one corresponding point.

The segment may be defined as an interval in the first domain. The interval may have a predefined length. The predefined length may be longer than a length of a feature of interest to be identified in the processed measurement.

The at least one segment may correspond to a single epoch of the biosignal. An epoch may be a segment of data that is expected (e.g., due to a stimulus provided, an instruction, or other occurrence affecting and precisely time-locked with the biosignal) to correspond to or comprise a feature of interest recorded in the biosignal. The epoch may be a part of the biosignal comprising at least one feature of interest. The epoch may be referred to as a trial. The epoch may be a time window having a predefined length. The predefined length may be longer than a length of a feature of interest to be identified in the processed measurement.

Sequence of Estimation Points

The at least one estimation point may comprise a sequence of estimation points determined by aggregating (e.g., applying the robust aggregation method to) all corresponding points in the segment of each of the one or more different decomposition sequences for the same frequency or frequency band.

Identifying Segment

The method may further comprise identifying (e.g., defining) the at least one segment in the at least one initial measurement or in the one, two or more decomposition sequences.

The at least one segment may be defined with respect to a first point in the first domain (e.g., a stimulus point), the first point being associated with a stimulus evoking or influencing the biosignal. The first point may be a point in time referred to as stimulus time point herein.

Alternatively, the at least one segment may be identified by matching a first point in the first domain (e.g., a stimulus point), the first point associated with a stimulus evoking or influencing the biosignal, to a second point (e.g., in the first domain) in the at least one initial measurement or the one, two or more decomposition sequences. The matching may be based on a first-domain-association between the first point and the and at least one initial measurement or based on a first-domain-association between the first point and the one, two or more decomposition sequences. The first point may correspond to the second point in the first domain.

The at least one segment may be defined with respect to the second point.

The method may comprise obtaining an indication of the first point, for example from a wireless mobile device such as the wireless mobile device 200.

The method may comprise obtaining an indication of one or more stimulus time points comprising a time-association between the one or more stimulus time points and the at least one initial measurement. A relative position of the stimulus time points with respect to the at least one initial measurement may be determined based on the time-association between the one or more stimulus time points and the at least one initial measurement. The relative position may be used to segment the (e.g., representation of the) at least one initial measurement into the segments. Each segment may be identified as a predefined time slot with reference to one or more of the stimulus time points. For example, each segment may be a time slot starting a first predefined time amount (e.g., SOms) before a stimulus time point and ending a second predefined time amount (e.g., 450 ms) after the stimulus time point.

The stimulus may be at least one of an auditory, a visual, a haptic or an olfactory stimulus provided to a human or animal, the body of which provides the biosignal.

Decompose Segments

Each identified segment of the at least one initial measurement may be individually decomposed into the joint frequency domain to obtain the segment of the decomposition sequence comprising the corresponding point.

Overlapping Measurements

The at least one initial measurement may comprise a first initial measurement of the biosignal in a first section of the first domain and a second initial measurement of the biosignal in the first section of the first domain. The first initial measurement may overlap the second initial measurement in the first domain.

(Wavelet) Transformation

The at least one initial measurement may be decomposed into the joint frequency domain by applying a transform having a varying resolution in the first domain (e.g., a varying first-domain resolution). The varying resolution may vary across frequencies. The at least one initial measurement may be decomposed into the joint frequency domain by applying a wavelet-based transform. The wavelet-based transform may be a Discrete Wavelet Transform, DWT. The wavelet-based transform may use a wavelet from the Debauchies-4, Symlet-5 or Coiflet-2 mother wavelet family. Each of the decomposition sequences may have an amplitude that corresponds to a magnitude of approximation or detail coefficients obtained by the DWT.

Joint Domain

In a first variant, the first domain may be a time domain, the joint frequency domain may be a time-frequency domain and the at least one initial measurement may optionally be a time-variable measured amplitude. In a second variant, the first domain may be a spatial domain, the joint frequency domain may be a space-frequency domain and the at least one initial measurement may optionally be a space-variable measured amplitude.

Combination of First and Second Medical Data Processing Methods

The method of the fourth aspect may be combined with the method of the first aspect or vice versa. For example, the at least one deviation obtained according to the method of the first aspect may be used as the corresponding points in the method of the second aspect. The robust aggregation method may be applied to the at least one deviation to determine the at least one estimation point. Alternatively, the at least one autoregressive model may be fitted to the at least one estimation point, the fitted function or the series of estimation points.

Use of Processed Measurement of First or Second Medical Data Processing Method for Feature Identification The processed measurement of the first medical data processing method or the processed measurement of the second medical data processing method may be used for identifying at least one feature indicative of the state of the user's brain health (e.g., as described above with reference to FIG. 3). The first medical data processing method and/or the second medical data processing method may further comprise identifying, in the processed measurement, at least one feature indicative of a state of the user's brain health.

The first medical data processing method and/or the second medical data processing method may further comprise determining an indicator of health, well-being or performance of a human or animal based on the identified at least one feature, wherein the human or animal has a body generating the biosignal. The human or animal may be a user of a wireless head-wearable sensor arrangement (e.g., the arrangement 100) comprising at least one sensor (e.g., the sensor 102) for generating the at least one initial measurement. The at least one feature indicative of the state of the user's brain health may be the feature described above with reference to FIG. 3. The at least one feature indicative of the state of the user's brain health may have predetermined (e.g., spatial, temporal and/or frequency) properties.

The at least one feature indicative of the state of the user's brain health may be identified (e.g., by the one or more processors 302) using a machine-learning based classifier. The indicator of health, well-being or performance of the user may be determined based on the identified at least one feature using a machine-learning based classifier.

Combination of First Medical Data Processing Method and/or Second Medical Data Processing Method with Time-Correction The first medical data processing method and/or the second medical data processing method may comprise one or more steps performed by the one or more processors 302 described above with reference to FIG. 3. The first medical data processing method and/or the second medical data processing method may comprise obtaining at least one measurement, at least one time-stamp allocated to the at least one measurement, and an indication on one or more stimulus time points, and may further comprise adjusting a time-association between the one or more stimulus time points and the at least one time-stamp or between the one or more stimulus time points and the at least one measurement, before identifying or determining the segment. Alternatively or additionally, the processed measurement may be time-corrected (e.g., as described above with reference to FIG. 3) before the segment is determined based on the time-corrected measurement.

The processed measurement of the first medical data processing method and/or the second medical data processing method may correspond to the "at least one measurement" used for determining the indicator of health, well-being or performance as described above with reference to FIG. 3. In other words, the one or more processors 302 may be configured to determine the processed measurement according to the first medical data processing method and/or the second medical data processing method, and determine the indicator of health, well-being or performance based on the processed measurement (e.g., by identifying the at least one feature indicative of a user's brain health in the processed measurement). The initial measurement of the first medical data processing method and/or the second medical data processing method may be time-corrected before the decomposition, as described above with reference to FIG. 3. In this case, the initial measurement may correspond to the "at least one measurement" referred to in the description of FIG. 3.

The processed measurement of the first medical data processing method and/or the second medical data processing method may be averaged across all segments comprised therein. The resulting averaged data may then be used for identifying the at least one feature.

Flowchart of Time-Synchronization Examples

FIG. 7 shows an illustration of four examples of how a time-synchronization procedure may be performed between a wireless head-wearable sensor arrangement (e.g., the arrangement 100) and a wireless mobile device (e.g., the device 200). The upper left illustration represents an embodiment of examples A), a) described above with reference to FIGS. 1 and 2. The bottom left illustration represents an embodiment of examples B), b) described above with reference to FIGS. 1 and 2. The upper right illustration represents an embodiment of examples C), c) described above with reference to FIGS. 1 and 2. The bottom right illustration represents an embodiment of examples D), d) described above with reference to FIGS. 1 and 2. As can be seen, the time information request message "Time info req" is sent from the wireless head-wearable sensor device to the wireless mobile device or vice versa. Therefore, the following description of FIG. 7 uses the same terminology used in the description of FIGS. 1 and 2.

The time information request message in the example of FIG. 7 includes the first time-stamp "TS1". The time information response message "Time info resp" is sent in the opposite direction to the time information request message and in the example of FIG. 7 comprises the third time-stamp "TS3" and the (e.g. indication of the) first difference "Diff1". As can be seen, a configuration message is sent from the same device that has previously sent the time information request message. In the example of FIG. 7, the configuration message comprises the second time-stamp "TS2" and either the indication of the adjustment amount or the adjustment (amount) instruction.

Figure 8:
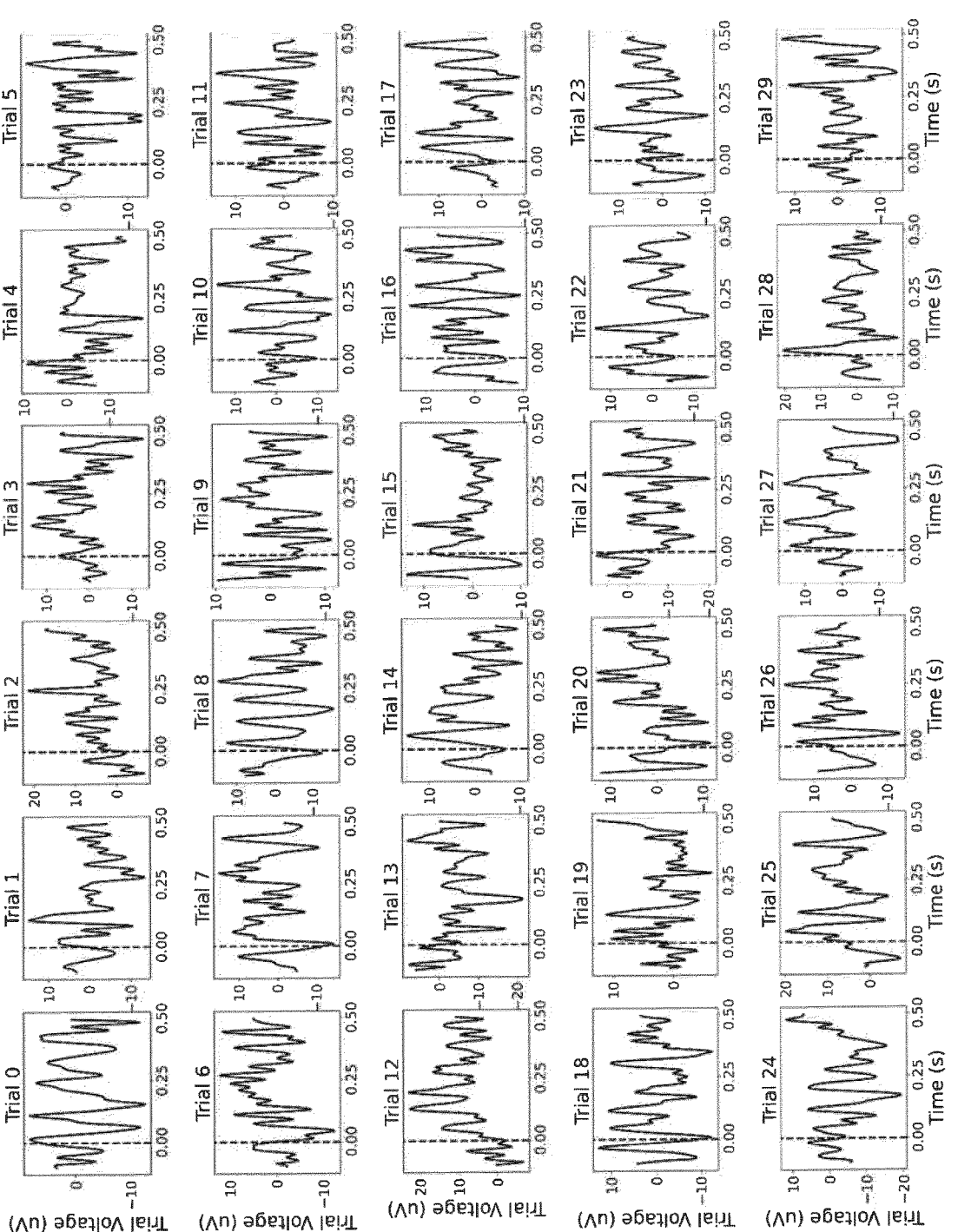
FIG. 8 shows a plurality of segments of a measurement of an EEG signal.

Examples of Segments of Measurement,
Decomposition Sequences of First Segment of
Measurement and Processed Measurements FIG. 8 shows an exemplary measurement of an EEG
signal of a user. The measurement has been segmented into
a total of 30 segments or "trials", for example as described
above with reference to FIG. 3, 5 or 6. The horizontal axes
denote time, whereas the vertical axes denote a measured
voltage or potential. As can be seen, each segment or trial
has been identified or defined as a predefined time slot with
reference to a certain time point, indicated in FIG. 8 as a
vertical dashed line in each of the segments. The certain time
point in this example may be the stimulus time point as
described herein.

Figure 9:
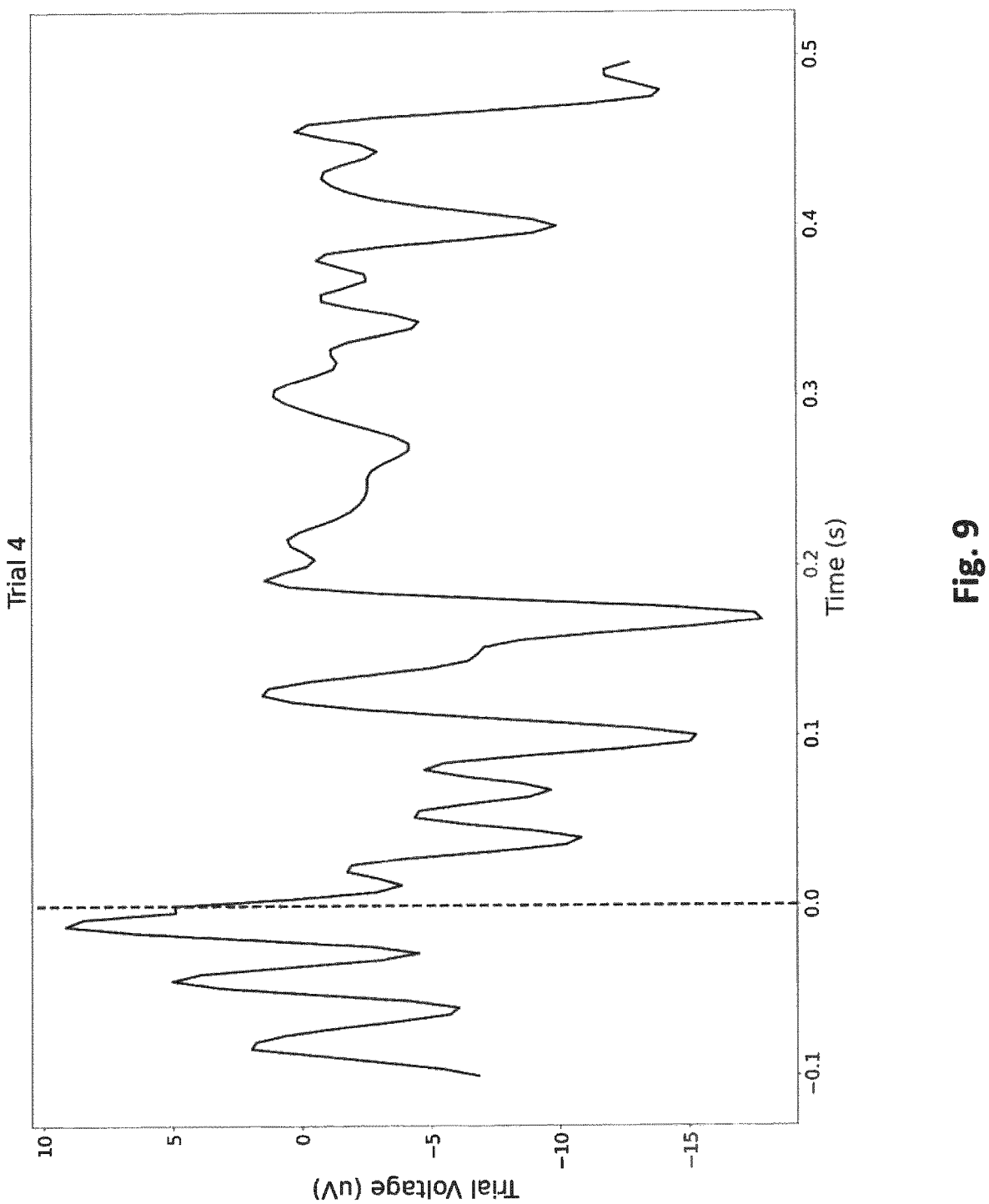
FIG. 9 shows one of the segments of FIG. 9 in an enlarged view.

FIG. 9 shows one of the segments of FIG. 8 in an enlarged
view. Again, the certain time point is indicated as a dashed
vertical line. It can be seen that the segment starts a first
predefined time before the certain time point and ends a
second, longer predefined time after the certain time point.
In the shown example, the first predefined time is 100 ms
and the second predefined time is 500 ms.

Figure 10:
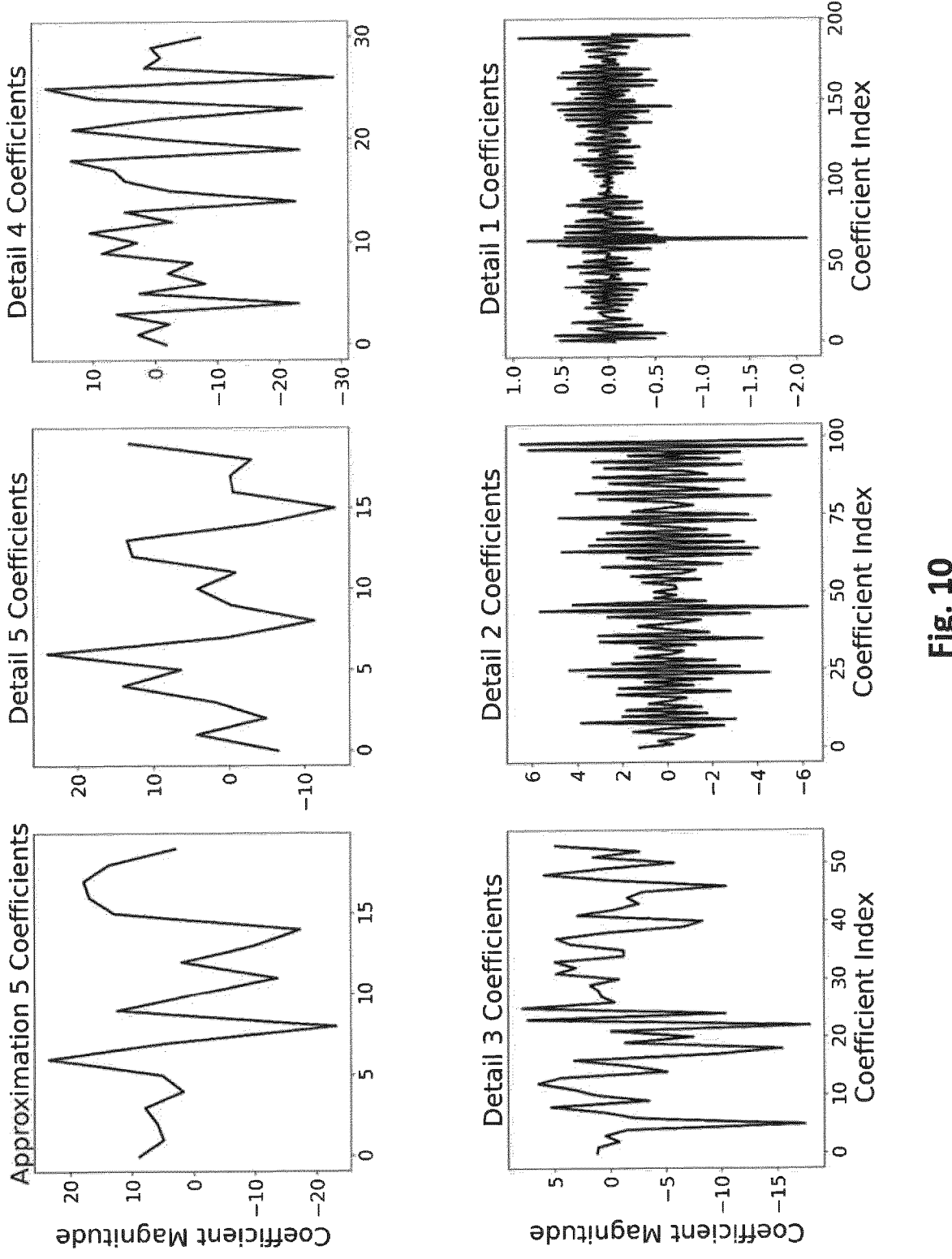
FIG. 10 shows a plurality of decomposition sequences of the segment of FIG. 9.

FIG. 10 shows a plurality of decomposition sequences of
the segment of FIG. 9. The decomposition sequences have
been obtained by decomposing the segment of FIG. 9 into a
time-frequency domain, for example in step 502 or step 602.
Each of the decomposition sequences shown in FIG. 10 has
an amplitude that corresponds to a magnitude of coefficients
obtained by the transformation used for the decomposition.
The decomposition sequences in the shown example have
been obtained by decomposing the segment of FIG. 9 using
a discrete wavelet transform. DWT. Thus, each of the
decomposition sequences shown in FIG. 10 have amplitudes
that correspond to magnitudes of coefficients obtained by the
DWT. As is known, applying a DWT to decompose a signal
from a first domain into a joint frequency domain results in
a set of detail coefficients and approximation coefficients for
the different layers of the DWT. The upper left illustration of
FIG. 10 shows the magnitudes of the approximation coef-
ficients of the fifth layer, the upper middle illustration shows
the magnitudes of the detail coefficients of the fifth layer,
and the upper right illustration shows the magnitudes of the
detail coefficients of the fourth layer. The bottom left illus-
tration shows the magnitudes of the detail coefficients of the
third layer, the bottom middle illustration shows the mag-
nitudes of the detail coefficients of the second layer, and the
bottom right illustration shows the magnitudes of the detail
coefficients of the first layer. Each of these illustrations
represents a separate decomposition sequence. The resolu-
tion of the DWT is higher for the first layer compared with
higher layers such as the second, third, fourth or fifth layer.

Figure 11:
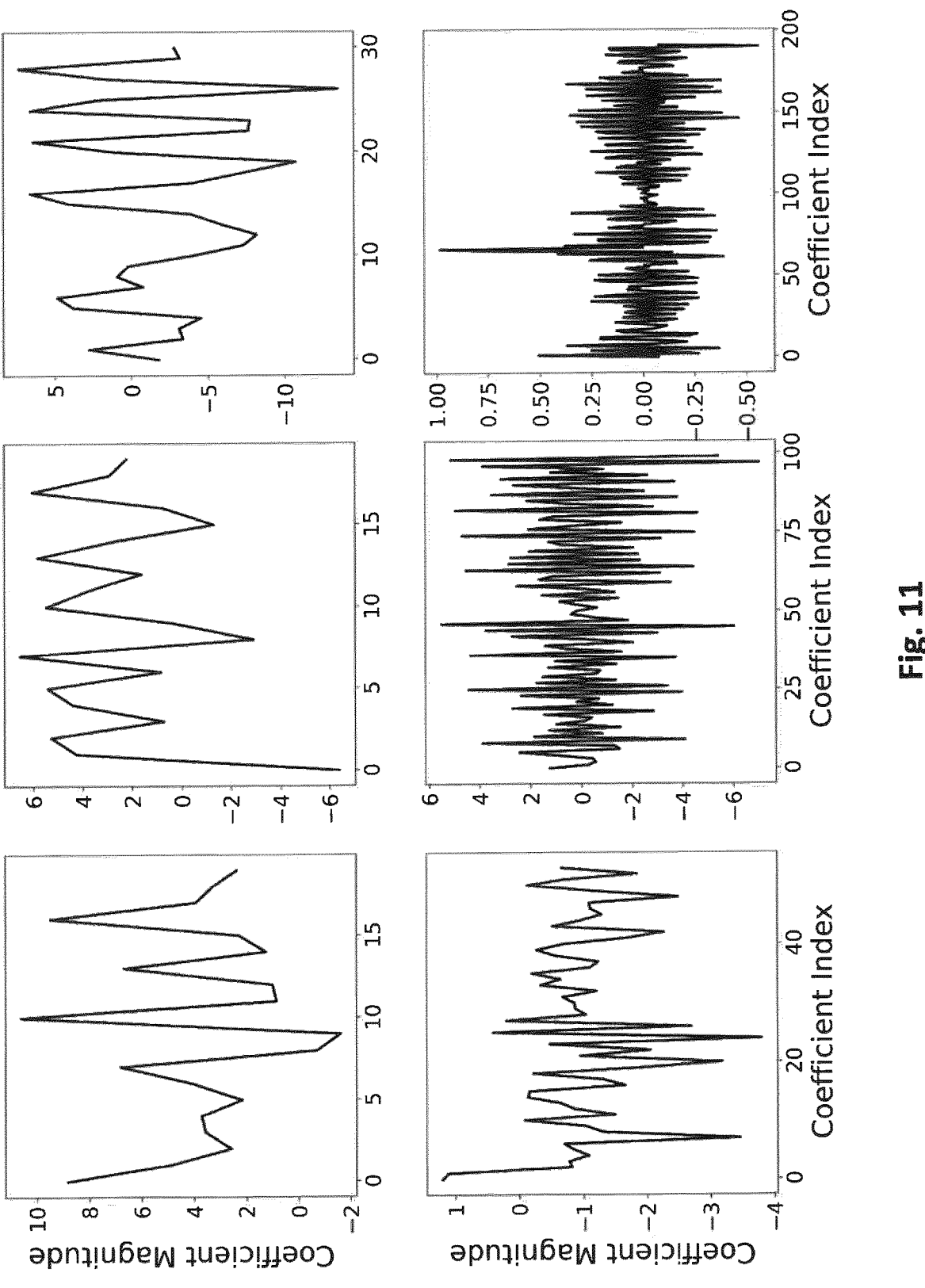
FIG. 11 shows an autoregressive model fitted to each of the decomposition sequences of FIG. 10.

FIG. 11 shows a result of fitting an autoregressive model
individually to each of the decomposition sequences shown
in FIG. 10. The upper left illustration shows the AR model
fitted to the decomposition sequence shown in the upper left
illustration of FIG. 10, the upper middle illustration shows
the AR model fitted to the decomposition sequence shown in
the upper middle illustration of FIG. 10, and so on. In the
example of FIG. 11, the fitted AR model is an AR(2) model.
Fitting the AR model to the decomposition sequences may
be performed as part of step 504. First-degree or second-
degree AR models have proven to yield the best results as
will be further discussed below.

Figure 12:
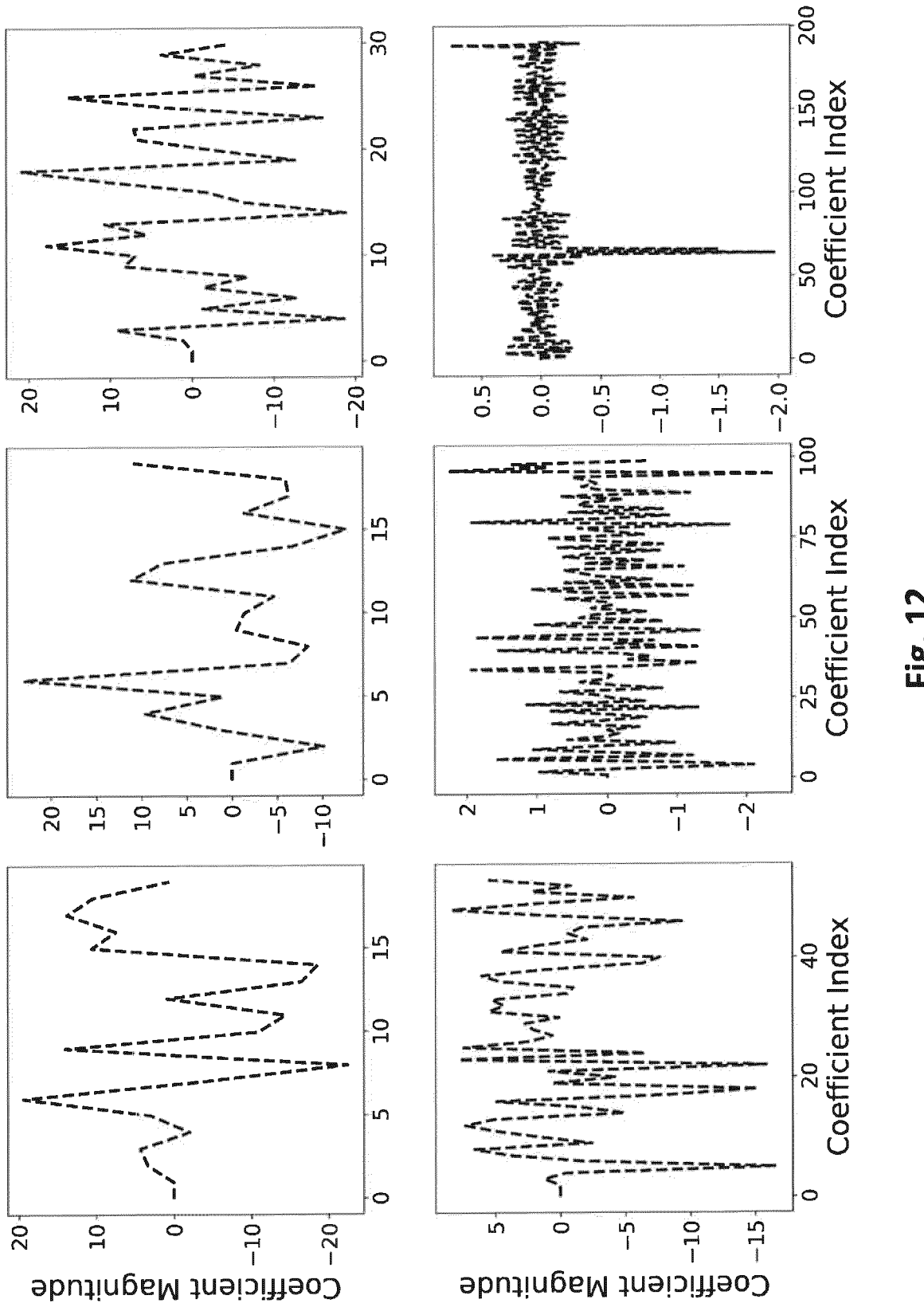
FIG. 12 shows residuals of the fitted autoregressive model of FIG. 11.

FIG. 12 shows residuals of the fitted autoregressive
model. The residuals may be determined as the at least one
deviation in step 506. The upper left illustration shows the
residuals of the fitted AR model of the upper left illustration of FIG. 11, the upper middle illustration shows the residuals
of the AR model of the upper middle illustration of FIG. 11,
and so on. The residuals may be the differences between the
fitted AR model and the decomposition sequence to which
the AR model is fitted. The residuals may then be used as the
processed measurement described herein. Alternatively, the
residuals may be recomposed as will now be discussed with
reference to FIG. 13.

Figure 13:
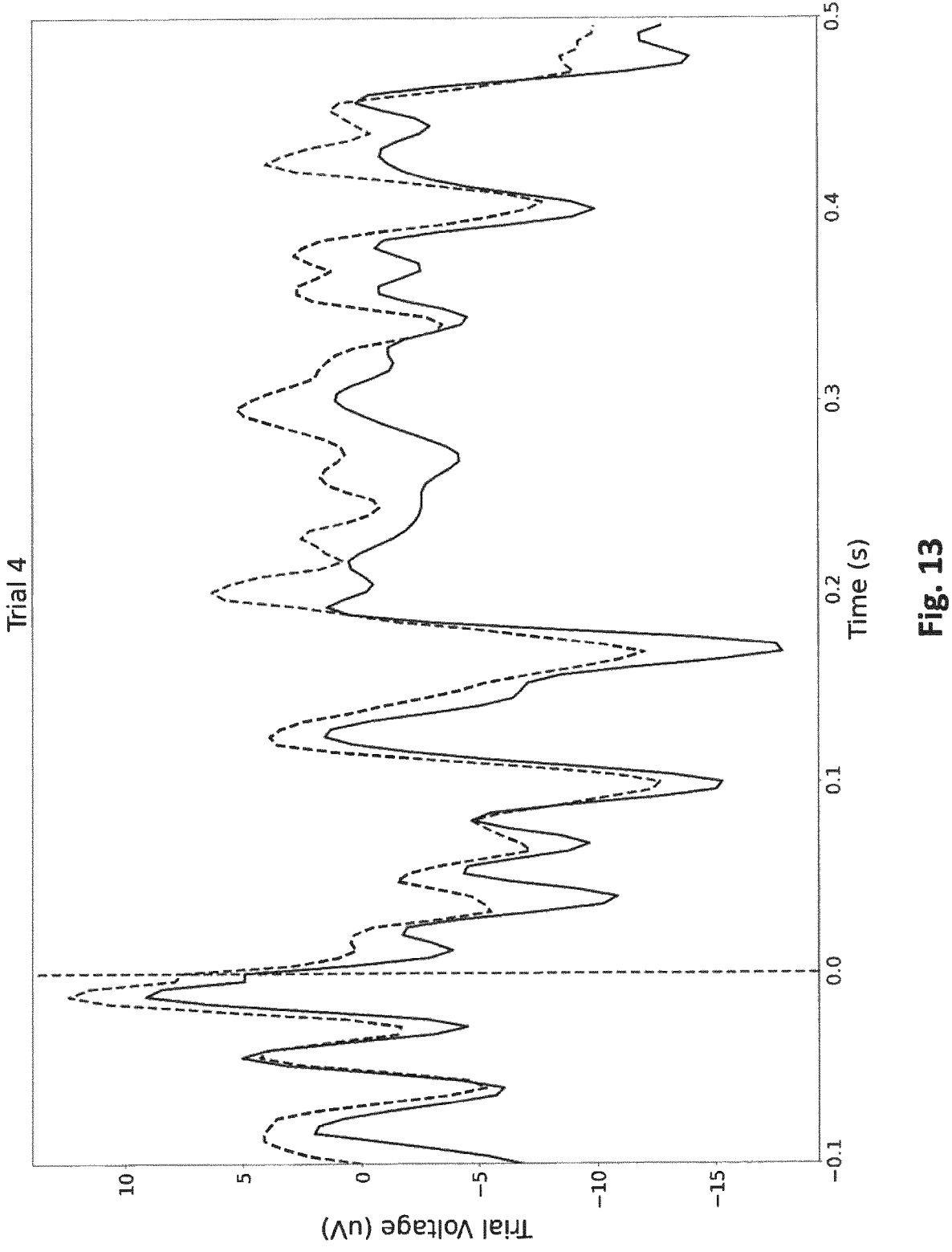
FIG. 13 shows the segment of FIG. 9 together with the residuals of FIG. 12 after recomposition.

FIG. 13 shows a comparison of the residuals shown in
FIG. 12, after being recomposed into the time domain. Also
shown is the original EEG signal of the segment used for
obtaining the recomposed residuals, as already discussed
with reference to FIG. 9 above. The illustration of FIG. 13
differs from FIG. 9 only in that the recomposed residuals are
added as a dashed line. The residuals shown in FIG. 13 have
been recomposed from the time-frequency domain illus-
trated in FIG. 12 into the time-domain by applying the
inverse of the DWT that was previously used for decom-
posing the segment of FIG. 9 into the decomposition
sequences of FIG. 10.

That is, the inverse of the transform was used for recom-
posing the residuals from the joint domain back into the first
domain. The recomposed residuals may be used as the
processed measurement described herein.

The procedure described with reference to FIGS. 8 to 13
may be performed for all of the segments of the EEG
measurement shown in FIG. 8. As a result, recomposed
residuals will be obtained for each segment. These recom-
posed residuals may then be averaged between (e.g., across)
the segments. The average may then be used as the pro-
cessed measurement described herein.

FIG. 14 shows three charts to clarify the outcome of the
processing described above.

In the upper illustration, an average of the signal of all
segments shown in FIG. 8 is drawn as a solid line. The
dashed line represents the recomposed residuals averaged
across all segments. It can be seen that the average of the
recomposed residuals follows the main course of the average
of the EEG signals of the segments. However, the average of
the recomposed residuals shows a different amplitude at
some of the peaks, for example at the peak at 100 ms and 200
ms.

Also shown in FIG. 14 is a result of combining the first
medical data processing method and the second medical data
processing method described herein. In this case, an M-es-
timator (Huber's T estimator) aggregation was applied to the
residuals of the fitted AR(2) model shown in FIG. 12, and
the aggregated result was recomposed into the first domain
by applying the inverse DWT. This was performed for all
segments. The average of all recomposed M-estimator
results is illustrated in the upper figure of FIG. 14 as a dotted
line. Also in this case, the amplitude of the average of the
recomposed M-estimator results differs from the averaged
EEG signals at some of the peaks.

The effect of the processing described with reference to
FIGS. 9-13 is even more apparent when referring to the
middle illustration of FIG. 14. This illustration shows the
standard deviation of the average of the signals of the
segments as a solid line, the standard deviation of the
average of the residuals as a dashed line, and the standard
deviation of the average of the recomposed M-estimator
results as a dotted line.

It is evident that the standard deviation of the average of
the signals is much larger than the standard deviation of the
average of the recomposed residuals or the standard devia-
tion of the average of the recomposed M-estimator results.
Put in other terms, the recomposed residuals and the recomposed M-estimator results may each be more consistent across different segments than the original EEG signal.

The bottom illustration of FIG. 14 shows an effect size of the average of the signals, the average of the recomposed residuals and the average of the recomposed M-estimator results. The effect size in this case has been calculated as the standardized mean (i.e. the mean divided by the standard deviation). That is, the curves shown in the bottom illustration of FIG. 14 correspond to a result of dividing the values of the curves of the upper illustration by the values of curves of the middle illustration.

Statistical comparisons commonly use a ratio of amplitude to variation. This ratio may be improved when performing the first and/or the second medical data processing method as described herein. In particular, when comparing the effect size of the averages of the recomposed residuals and the recomposed M-estimator results to averages of the EEG signal in the bottom illustration of FIG. 14, and also in view of the upper illustration in FIG. 14, it is evident that the processing described above for FIGS. 8 to 13 results in higher effect sizes and peaks near the time-points 100 ms, 1S0 ms and 250 ms. The value of the processed measurement at each of these time-points may be the feature of interest. One may say that in this example, the statistical efficiency of the processed measurement is improved compared with the initial measurement

GENERAL REMARKS

The processing in accordance with the first medical data processing method, the processing in accordance with the second medical data processing method or a combination thereof may result in a processed measurement which is more consistent across different segments. Generally speaking, the larger the consistency of a measurement across different segments of a measurement, the more reliable a detection of a feature in the measurement will be. Therefore, the techniques described herein may enable a more reliable detection of a feature of interest (e.g., an evoked potential) in a measurement.

The at least one feature may be identified (e.g., by the system 300) based on a temporal property of the feature with respect to the at least one time-stamp. The at least one feature may be identified in a time slot having a predefined relation to the at least one time-stamp. The at least one time-stamp may denote a time of a stimulus time point or have a predefined temporal difference thereto, wherein the segments described herein may be defined or identified based on the stimulus time point. Each of the segments may comprise the at least one feature. Using the techniques and methods disclosed herein may ensure that the at least one feature occurs in each of the segments at a same first-domain position. This may improve reliability of the identification of the at least one feature and decrease processing effort.

The techniques and methods disclosed herein may provide for a compensation of a time misalignment between a second clock of a stimulus-providing wireless mobile device (e.g., the device 200) and a first clock of a measurement-generating sensor arrangement (e.g., the arrangement 100). This may ensure that the at least one time-stamp allocated to the at least one measurement complies with both the first and the second clock. Thereby, it can be further ensured that the at least one feature occurs in each of the segments, defined based on the at least one time-stamp, at a same first-domain position.

The techniques and methods disclosed herein may also provide for a compensations of a clock drift between the first clock and the second clock. This may ensure that the one or more stimulus time points have a known position in the at least one (e.g., initial) measurement. This may enable determining the segments in a reliable manner with respect to the stimulus time points. It may therefore be ensured that the at least one feature occurs in each of the segments at a same first-domain position.

As indicated above, the first medical data processing method may be combined with the second medical data processing method. The methods may comprise one of more additional steps performed by the computing system 300, the device 200 or the arrangement 100. Similarly, the computing system 300 may be configured to perform the first medical data processing method and/or the second medical data processing method in addition to the procedure described above with reference to FIG. 3. Other variants are also possible without departing from the scope of the present disclosure.

What is claimed is:

1. A wireless head-wearable sensor arrangement for sending medical data to a wireless mobile device, the wireless head-wearable sensor arrangement comprising:

at least one sensor configured to generate at least one measurement of a biosignal of a user wearing the wireless head-wearable sensor arrangement;

a first wireless interface;

a first clock; and a first processor configured to:

perform a time-synchronization procedure to synchronize the first clock with a second clock of the wireless mobile device or to instruct synchronization of the second clock of the wireless mobile device with the first clock;

after having performed the time-synchronization procedure, obtain, from the at least one sensor, the at least one measurement of the biosignal of the user wearing the wireless head-wearable sensor arrangement, allocate at least one time-stamp to the obtained at least one measurement, and send the medical data via the first wireless interface to the wireless mobile device, the medical data comprising a representation of the at least one measurement and the at least one time-stamp allocated to the at least one measurement, wherein the first processor is configured to perform the time-synchronization procedure by:

sending a time information request message to the wireless mobile device via the first wireless interface, the time information request message comprising a first time-stamp of a time of sending the time information request message; and receiving a time information response message from the wireless mobile device via the first wireless interface, the time information response message comprising synchronization information, wherein the first processor is configured to synchronize the first clock by adjusting the first clock based at least on the synchronization information, wherein the first processor is configured to, after having adjusted the first clock, send a configuration message to the wireless mobile device via the first wireless interface, the configuration message comprising at least one of a second time-stamp of a time of sending the configuration message and an indication of an adjustment amount of the first clock.

2. The arrangement of claim 1, wherein the synchronization information is dependent on at least the first time-stamp, and wherein the synchronization information comprises an indication of a first time difference between the time of sending the time information request message as indicated by the first time-stamp and a time of receiving the time information request message.

3. The arrangement of claim 2, wherein the synchronization information comprises a third time-stamp of a time of sending the time information response message, and wherein the first processor is configured to determine a synchronization deviation between the first clock and the second clock based on the first time difference and a second time difference between the time of sending the time information response message as indicated by the third time-stamp and a time of receiving the time information response message.

4. The arrangement of claim 3, wherein the first processor is configured to determine a round-trip latency based on the first time difference and the second time difference, and determine the synchronization deviation further based on the round-trip latency.

5. The arrangement of claim 4, wherein the first processor is configured to synchronize the first clock by adjusting the first clock such that the determined synchronization deviation is compensated, and wherein the first processor is configured to perform multiple cycles of sending the time information request message and receiving the time information response message, determine the synchronization deviation for each pair of time information request message and time information response message, and adjust the first clock such that a smallest of the determined synchronization deviations is compensated or such that an average of the determined synchronization deviations is compensated.

6. A wireless mobile device for receiving medical data from a wireless head-wearable sensor arrangement, the wireless mobile device comprising:
   a second wireless interface;
   a second clock; and
   a second processor configured to:
      perform a time-synchronization procedure to synchronize the second clock with a first clock of the wireless head-wearable sensor arrangement or to instruct synchronization of the first clock of the wireless head-wearable sensor arrangement with the second clock; and
      after having performed the time-synchronization procedure, receive the medical data from the wireless head-wearable sensor arrangement via the second wireless interface and send the medical data to a computing system, the medical data comprising a representation of at least one measurement of a biosignal of a user wearing the wireless head-wearable sensor arrangement and at least one time-stamp allocated to the at least one measurement,
      wherein the second processor is configured to:
      receive a time information request message from the wireless head-wearable sensor arrangement via the second wireless interface, the time information request message comprising a first time-stamp of a time of sending the time information request message;
      determine synchronization information based at least on information comprised in the time information request message; and
      send a time information response message to the wireless head-wearable sensor arrangement via the second wireless interface, the time information response message comprising the synchronization information, wherein the second processor is configured to, after having sent the time information response message, receive a configuration message from the wireless head-wearable sensor arrangement via the second wireless interface, the configuration message comprising an indication of an adjustment amount of the first clock and a second time-stamp of a time of sending the configuration message.

7. The device of claim 6, wherein the synchronization information is dependent on at least the first time-stamp, and wherein the synchronization information comprises an indication of a first time difference between the time of sending the time information request message as indicated by the first time-stamp and a time of receiving the time information request message.

8. The device of claim 7, wherein the synchronization information comprises a third time-stamp of a time of sending the time information response message, and wherein the second processor is configured to determine a synchronization deviation between the first clock and the second clock based on the first time difference and a second time difference between the time of sending the time information response message as indicated by the third time-stamp and a time of receiving the time information response message.

9. The device of claim 6, wherein:
   the second processor is configured to receive a time synchronization request message from the wireless head-wearable sensor arrangement via the second wireless interface and to start performing the time-synchronization procedure in response to receiving the time synchronization request message;
   the time synchronization request message comprises a fourth time-stamp of a time of sending the time synchronization request message and the second processor is configured to pre-adjust the second clock based on the time of sending the time synchronization request message as indicated by the fourth time-stamp, before performing the time-synchronization procedure; and
   the second processor is configured to pre-adjust the second clock if the time indicated by the fourth time-stamp deviates more than a predefined amount from a time of receiving the time synchronization request message.

10. The device of claim 6, wherein:
   the second processor is configured to send a time synchronization request message to the wireless head-wearable sensor arrangement via the second wireless interface to trigger the wireless head-wearable sensor arrangement to start performing the time-synchronization procedure;
   the time synchronization request message comprises a fourth time-stamp of a time of sending the time synchronization request message and instructs the head-wearable sensor arrangement to pre-adjust the first clock based on the time of sending the time synchronization request message as indicated by the fourth time-stamp, before performing the time-synchronization procedure; and
   the time synchronization request message instructs the wireless head-wearable sensor arrangement to pre-adjust the first clock if the time indicated by the fourth time-stamp deviates more than a predefined amount from a time of receiving the time synchronization request message.

11. A computing system for receiving medical data from a wireless mobile device, the computing system comprising one or more processors configured to:

receive, from the wireless mobile device comprising a second clock, medical data comprising a representation of at least one measurement of a biosignal of a user wearing a wireless head-wearable sensor arrangement and at least one time-stamp allocated to the at least one measurement, the wireless head-wearable sensor arrangement comprising a first clock; and determine, based on the representation of the at least one measurement and the at least one time-stamp allocated to the at least one measurement, an indicator of health, well-being or performance of the user of the wireless head-wearable sensor arrangement, wherein the one or more processors are configured to receive, from the wireless mobile device, an indication of an adjustment amount of either the first clock or the second clock used for synchronizing the first clock or the second clock, or an adjustment amount instruction used for synchronizing the first clock or the second clock, and wherein the one or more processors are configured to determine the indicator of health, well-being or performance of the user further based on the indication of the adjustment amount or the adjustment amount instruction.

12. The system of claim 11, wherein the one or more processors are configured to receive a time-association between the adjustment amount and the at least one measurement, or between the adjustment amount instruction and the at least one measurement from the wireless mobile device, and wherein the one or more processors are configured to determine the indicator of health, well-being or performance of the user further based on the time-association.

13. The system of claim 11, wherein the one or more processors are configured to:

receive, from the wireless mobile device, an indication of one or more stimulus time points at which at least one stimulus is provided to the user, wherein the one or more processors are configured to determine the indicator of health, well-being or performance of the user further based on the indication of the one or more stimulus time points, and wherein the indication of the one or more stimulus time points comprises a time-association between the one or more stimulus time points and the at least one measurement.

14. The system of claim 11, wherein the one or more processors are configured to receive, from the wireless mobile device, user data describing a user input received via a user interface of the wireless mobile device, and wherein the one or more processors are configured to determine the indicator of health, well-being or performance of the user further based on the user data, and wherein the user data comprises a time-association between one or more time points of received user input and the at least one measurement.

15. The system of claim 11, wherein the one or more processors are configured to determine at least one time-adjusted measurement by performing one or more of:

adjusting at least a part of the representation of the at least one measurement in time based on at least some information received from the wireless mobile device, and determining the indicator of health, well-being or performance of the user of the wireless head-wearable sensor arrangement based on the at least one time-adjusted measurement; and adjusting the at least one time-stamp allocated to the at least one measurement in time based on the at least some information received from the wireless mobile device, and determining the indicator of health, well-being or performance of the user of the wireless head-wearable sensor arrangement further based on the at least one time-adjusted time-stamp.

16. A medical data processing system comprising at least two of the following:

a computing system;

a wireless head-wearable sensor arrangement; or a wireless mobile device comprising:

a second wireless interface;

a second clock; and a second processor configured to:

perform a time-synchronization procedure to synchronize the second clock with a first clock of the wireless head-wearable sensor arrangement or to instruct synchronization of the first clock of the wireless head-wearable sensor arrangement with the second clock; and after having performed the time-synchronization procedure, receive medical data from the wireless head-wearable sensor arrangement via the second wireless interface and send the medical data to the computing system, the medical data comprising a representation of at least one measurement of a biosignal of a user wearing the wireless head-wearable sensor arrangement and at least one time-stamp allocated to the at least one measurement, wherein the second processor is configured to perform the time-synchronization procedure by:

sending a time information request message to the wireless head-wearable sensor arrangement via the second wireless interface, the time information request message comprising a first time-stamp of a time of sending the time information request message; and receiving a time information response message from the wireless head-wearable sensor arrangement via the second wireless interface, the time information response message comprising synchronization information, wherein the second processor is configured to synchronize the second clock by adjusting the second clock based at least on the synchronization information, and wherein the second processor is configured to, after having adjusted the second clock, send a configuration message to the wireless head-wearable sensor arrangement via the second wireless interface, the configuration message comprising at least one of a second time-stamp of a time of sending the configuration message and an indication of an adjustment amount of the second clock.

* * * * *